(12) United States Patent
Abebe et al.

(10) Patent No.: US 11,141,418 B1
(45) Date of Patent: Oct. 12, 2021

(54) METHODS AND COMPOSITIONS FOR KRAS INHIBITORS

(71) Applicant: The Board of Regents, The University of Texas System, Austin, TX (US)

(72) Inventors: Alemayehu Gorfe Abebe, Austin, TX (US); Michael J. McCarthy, Austin, TX (US); Cynthia V. Pagba, Austin, TX (US); Priyanka Prakash Srivastava, Austin, TX (US)

(73) Assignee: THE BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/449,785

(22) Filed: Jun. 24, 2019

Related U.S. Application Data

(60) Provisional application No. 62/688,626, filed on Jun. 22, 2018.

(51) Int. Cl.
*A61K 31/519* (2006.01)

(52) U.S. Cl.
CPC .................................. *A61K 31/519* (2013.01)

(58) Field of Classification Search
CPC .................................................... A61K 31/519
See application file for complete search history.

(56) References Cited

PUBLICATIONS

Sikora, Current Science 2001, 81(5), 549-554.*
Schmutzler et al. European Journal of Endocrinology 2000, 143, 15-24.*
McCarthy et al., (2017). Prediction and Initial Characterization of K-Ras Inhibitors. The 61st Biophysical Society Annual Meeting, New Orleans, Louisiana, Feb. 11-15.
McCarthy et al., (2016). Prediction and Initial Characterization of K-Ras Inhibitors. The ACS 72nd Annual Southwest Regional Meeting, Galveston, Texas, Nov. 10-13.
McCarthy, Structure-based drug design of high affinity KRAS inhibitors, Feb. 26, 2018.
McCarthy, M. (2016). Prediction and initial characterization of K-Ras inhibitors. Cell and Regulatory Biology Retreat, Navasota, Texas, Apr. 21-22.
McCarthy et al., (2016). Prediction and Initial Characterization of K-Ras Inhibitors. Fragment Based Drug Discovery Conference, Houston, Texas, May 24.
McCarthy, M. (2014). Identifying Drug-Like Ligands for Mutant Kras. Cell and Regulatory Biology Retreat, Navasota, Texas. Apr. 23-24.
McCarthy et al., (2015). Designing Molecules to Inhibit Oncogenic Mutant K-Ras Using Computational, Cell-biological and Biophysical Approaches. FASEB Science Research Conference: Regulation and Function of Small GTPases, West Palm Beach, Florida, Jun. 7-12.

* cited by examiner

*Primary Examiner* — Svetlana M Ivanova
(74) *Attorney, Agent, or Firm* — Hylton-Rodic Law PLLC

(57) ABSTRACT

In one aspect, the disclosure relates to compounds that are inhibitors of KRAS, and the disclosed compounds are allosteric inhibitors of KRAS which render them extremely useful for therapeutic intervention in a variety of disorders and diseases in which inhibition of DHODH can be clinically useful, e.g., cancer. In various aspects, the disclosed compounds are substituted 7-(piperazin-1-yl)pyrazolo[1,5-a]pyrimidine analogs. In further aspects, the disclosed compounds can be used in methods of treating a cancer. This abstract is intended as a scanning tool for purposes of searching in the particular art and is not intended to be limiting of the present disclosure.

7 Claims, 13 Drawing Sheets

Compound 11

Compound 12

Compound 13

METHODS AND COMPOSITIONS FOR KRAS INHIBITORS

CROSS-REFERENCE TO RELATED APPLICATIONS

This application claims the benefit of U.S. Provisional Application No. 62/688,626, filed on Jun. 22, 2018, which is incorporated herein by reference in its entirety.

BACKGROUND

Somatic mutations in RAS proteins are associated with about 16% of all human cancers (1, 2). KRAS is the most frequently mutated RAS isoform, accounting for 85% of all RAS-related cancers (1, 2). Cellular KRAS is tethered to the inner surface of the plasma membrane by a farnesylated polybasic lipid anchor (3), and cycles between active guanosine tri-phosphate (GTP)- and inactive guanosine di-phosphate (GDP)-bound conformational states (4). GTPase activating proteins (GAPs) facilitate hydrolysis of GTP by KRAS while guanine nucleotide exchange factors (GEFs) catalyze GDP dissociation (4-6). Upon activation by receptor tyrosine kinases such as epidermal growth factor (EGF) receptors, GEFs are recruited to KRAS and initiate exchange of GDP for GTP. Active KRAS interacts with effectors such as Raf in the MAPK pathway and PI3K in the AKT pathway (7), driving cell growth and proliferation (8, 9). In a regulated RAS cycle, signaling is turned off upon GTP hydrolysis. Oncogenic mutations that impair its GAP-mediated or intrinsic GTPase activity render KRAS constitutively active and thereby cause uncontrolled cell growth/proliferation leading to cancer (1, 2). Mutant KRAS is therefore a highly sought-after anticancer drug target (10, 11).

Despite decades of efforts, however, drugging KRAS (and RAS proteins in general) remains an unrealized goal (12). Among the many challenges, conservation of the nucleotide-binding site among a diverse group of small GTPases (4, 13), and the high (picomolar) affinity of RAS for its endogenous ligands GDP or GTP, are arguably the most significant. These issues made competitive inhibition impractical and avoiding off-target effects difficult. Thus, along with efforts at indirect RAS inhibition by targeting its interaction partner proteins (14, 15) or membrane localization (16, 17), development of direct allosteric KRAS inhibitors is currently a major focus of many laboratories (18). Proof-of-principle studies have established the allosteric nature of RAS (11, 19, 20), and discovered several allosteric small-molecule KRAS binders (21-25). Moreover, a number of recent reports described molecular fragments (23), small-molecules (18, 24-26), peptidomimetics (27, 28) and monobodies (29) that bind KRAS and modulate its functions in various ways. While this paints an optimistic picture of the prospects of allosteric KRAS inhibition, to the best of our knowledge none of these compounds has made it to clinical trial. Recent efforts toward developing covalent GDP analogues (30) or other small-molecule ligands (31) targeting G12C mutant KRAS may have a better chance of eventually treating specific tumor types (18). However, their application is likely limited to a few cancer cases such as small cell lung cancer (10). The most important mutations in KRAS including G12D, G12V, G13D and Q61H that are critical in biliary tract, small intestine, colorectal, lung and pancreas cancers (2, 10), but these will likely not be addressable except using non-covalent allosteric inhibition to target them. Together, these four mutations appear to account for greater than 78% of all KRAS-associated cancers (10).

Despite advances in treatment of cancer and therapeutic agents targeting specific proteins believed to be involved in onset and progression of cancer, there is still a scarcity of compounds that are both potent, efficacious, and selective inhibitors of the KRAS protein and also effective in the treatment of disorders and diseases in which the KRAS is involved. These needs and other needs are satisfied by the present disclosure.

SUMMARY

In accordance with the purpose(s) of the present disclosure, as embodied and broadly described herein, the disclosure, in one aspect, relates to substituted 7-(piperazin-1-yl)pyrazolo[1,5-a]pyrimidine analogs that inhibit KRAS, pharmaceutical compositions comprising same, and methods of treating disorders of uncontrolled cellular proliferation, such as a cancer, using same. In a further aspect, the disclosed compounds bind to KRAS with sub-micromolar affinity, modulate exchange factor activity, disrupt effector Raf binding, significantly reduce signal transduction through mutant KRAS, and inhibit cancer cell growth.

In various aspects, the present disclosure pertains to a pharmaceutical composition comprising a compound having a formula represented by a formula:

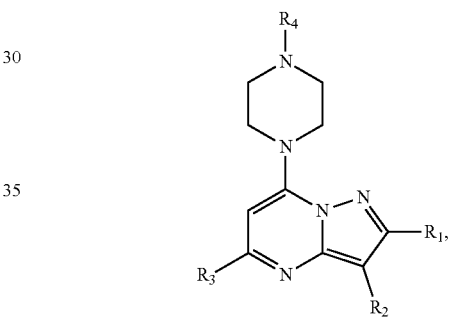

wherein $R_1$ is C1-C6 alkyl; wherein each of $R_2$ and $R_3$ is independently a C1-C8 alkyl, cycloalkyl, heterocycloalkyl, aryl, or heteroaryl; and wherein $R_4$ is —(C1-C6 alkyl), —(C1-C6 alkanediyl)-SF$_5$, —(C1-C6 alkanediyl)-OH, —(C1-C6 alkanediyl)-SH, —(C1-C6 alkanediyl)-NH$_2$, —(C1-C7 haloalkyl), —C1-C7 hydroxyalkyl, —(C1-C6 alkyl)(C=O)R$_5$; wherein R$_5$ is hydroxy, amino, —O(C1-C6 alkyl), —O(C1-C6 haloalkyl), —NH(C1-C6 alkyl), or —N(C1-C6 alkyl)$_2$, or a pharmaceutically acceptable salt thereof, and a pharmaceutically acceptable carrier.

In a further aspect, the present disclosure pertains to methods for the treatment of a disease or disorder in a mammal comprising the step of administering to the mammal a therapeutically effective amount of a disclosed pharmaceutical composition.

Also disclosed are methods for the treatment of a cancer in a mammal comprising the step of administering to the mammal a therapeutically effective amount of a disclosed pharmaceutical composition.

Also disclosed are kits comprising a therapeutically effective amount of a disclosed pharmaceutical composition; optionally at least one agent known to treat a cancer; and instructions for treating a cancer.

Also disclosed are methods for manufacturing a medicament comprising combining at least one disclosed compound with a pharmaceutically acceptable carrier or diluent.

Also disclosed are uses of at least one disclosed compound in the manufacture of a medicament for the treatment of a disease or disorder in a mammal such as a cancer.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

(FIG. 1A) Structure of the catalytic domain of KRAS used for the virtual screening. Lobe1 (residues 1-86) and lobe2 (residues 87-166) are highlighted in different colors, as well as switches 1 (residues 30-40) and 2 (residues 60-75). The location of the target allosteric pocket p1 is indicated. (FIG. 1B) Chemical structure of compound 11. (FIG. 1C) Predicted binding pose of compound 11, with the key residues that make polar or vdW contacts with the ligand labeled. (FIG. 1D) Microscale thermophoresis (MST) experiments indicating direct binding of compound 11 to KRAS, along with dissociation constants ($K_D$) derived from the curves. Changes in fluorescence upon titration of 50 μM KRAS with increasing concentration of compound are shown: $KRAS^{WT}$ (red), $KRAS^{G12C}$ (green), $KRAS^{G12D}$ (purple) and $KRAS^{Q61H}$ (blue), each bound to the non-hydrolyzable GTP analogue, guanylyl imidodiphosphate (GNP). The same experiments indicated no binding to GDP-bound $KRAS^{G12D}$ and $KRAS^{WT}$ as well as Rap1B, which was used as control.

(FIG. 2A) Fluorescence polarization of $^{BGTP-\gamma-S}$KRAS (0.5 μM) as a function of a varying concentration of GST-Raf$^{RBD}$ in the absence (red) and presence (blue) of 1 μM compound 11. Shown above the curves is the $K_D$ for KRAS-Raf$^{RBD}$ binding obtained by fitting the data to $$P = P1 + (P2 - P1)\frac{Kd + c + x - \sqrt{(Kd + c + x)^2 - 4*c*x}}{2},$$

where P1 is polarization of free KRAS, P2 is polarization of Raf-bound KRAS, c is the total concentration of KRAS, and x the total concentration of Raf$^{RBD}$. (FIG. 2B) Amount of GFP-KRAS$^{G12D}$ pulled down by GST-Raf$^{RBD}$ after treatment of cell lysates with compound at the concentrations indicated (representative Westerns are shown at the top). The RBD sequence length was 1-149 and 51-131 in the fluorescence polarization and pull-down assays, respectively. (FIG. 2C) GFP fluorescence lifetime from FLIM-FRET using cells expressing GFP-KRAS$^{G12D}$ alone or with RFP-Raf, with or without treatment by μM compound 11. Data are shown as mean ±S.E; significance estimated by one-way analysis of variance.

(FIG. 5A) Chemical structure of compounds 12, an analogue of 11 lacking the terminal methyl alcohol functional group. (FIG. 5B) Predicted binding pose of compound 12. (FIG. 5C) p-ERK and p-cRaf levels in BHK cells expressing KRAS$^{G12D}$ treated with indicated concentrations of compound 12 or vehicle. (FIG. 5D) Proliferation profile of lung cancer cells upon treatment with increasing concentration of compound 12, monitored by a CyQuant assay. Data are averages over three independent experiments and error bars represent standard error. (FIG. 5E) GFP fluorescence lifetime from FLIM-FRET using cells expressing GFP-KRAS$^{G12D}$ alone or together with RFP-cRaf, with or without treatment with 2 μM compound 12.

(FIG. 6A) Chemical structure of compound 13, an analogue of 11 without a benzene on the pyrimidine core. (FIG. 6B) Predicted binding pose of compound 13. (FIG. 6C) Shows representative fluorescence intensity data obtained from MST experiments on KRAS mutants and control. See legend of FIGS. 2A-2C for additional details. The inset to the right of the graph shows the calculated KD values obtained from the fluorescence intensity data. (FIG. 6D) Fluorescence polarization of $^{BGTP-\gamma-S}$KRAS (0.5 μM) with increasing concentration of GST-Raf$^{RBD}$ in the absence (red) and presence (green) of 20 μM compound 13. (FIG. 6E) Level of GFP-KRAS$^{G12D}$ pulled down by GST-Raf$^{RBD}$ after treatment of whole cell lysates with 10 μM of compound 13 (representative Western blots are shown at the top). The RBD sequence length was 1-149 in the fluorescence polarization assay (FIG. 6D) and 51-131 in the pull-down assay (FIG. 6E). (FIG. 6F) Intrinsic (red) and SOS-mediated (blue) nucleotide release rates were determined. Briefly, fluorescence intensity data obtained in a mixture of 0.5 μM KRAS (and SOS), 100 μM GTP and 0 or 50 μM of compound 13 (top), derived from the changes in during the reaction $KRAS^{BGDP}+GTP \rightarrow KRAS^{GTP}+$ BGDP (bottom). Rates were calculated using single exponential fits starting from 120 s, and are show in the inset to the right of the graph.

Figure 1A:
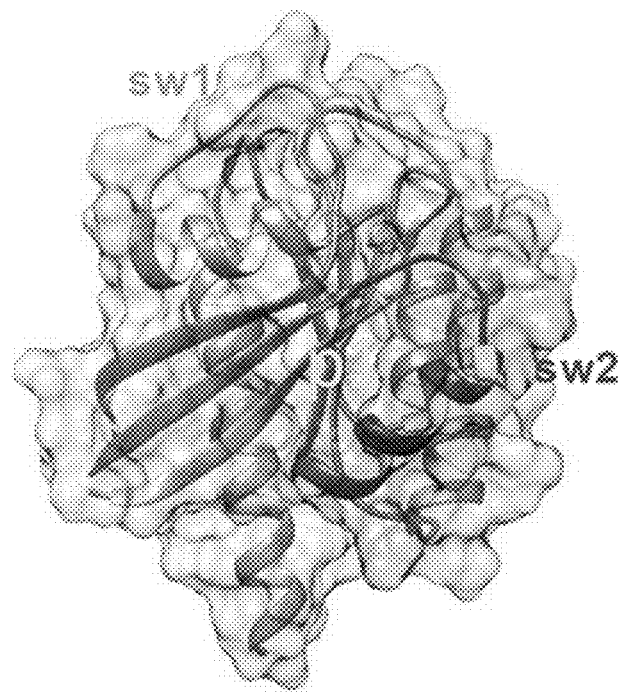
FIGS. 1A-1D show representative data for the predicted binding mode and measured affinity of disclosed compound 11 to KRAS.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a unimolecular nanoparticle," "a nanocluster," or "a biomimetic vesicle," including, but not limited to, two or more such unimolecular nanoparticles, nanoclusters, or biomimetic vesicles, including combinations of unimolecular nanoparticles, nanoclusters, or biomimetic vesicles, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "KRAS" refers to is a gene in humans with a cytogenetic location of 12p12.1 and a molecular location of base pairs 25,204,789 to 25,251,003 on chromosome 12 (*Homo sapiens* Annotation Release 109, GRCh38.p12). The gene structure in humans comprises 6 exons. KRAS gene encodes the human cellular homolog of a transforming gene isolated from the Kirsten rat sarcoma virus. KRAS alternates between an inactive form bound to GDP and an active form bound to GTP. Activated by a guanine nucleotide-exchange factor (GEF) and inactivated by a GTPase-activating protein (GAP). Interaction with SOS1 promotes exchange of bound GDP by GTP. Cellular KRAS is tethered to the inner surface of the plasma membrane by a farnesylated polybasic lipid anchor (3), and cycles between active guanosine tri-phosphate (GTP)- and inactive guanosine di-phosphate (GDP)-bound conformational states (4). KRAS has also been referred to as K-RAS, K-Ras, K-ras, Kras, K-RAS4B, K-Ras4B, K-ras4B, Kras4B, K-RAS4B, C-K-RAS, c-K-ras protein, c-K-ras2 protein, c-Kirsten-ras protein, cellular c-Ki-ras2 proto-oncogene, K-ras p21 protein, KI-RAS, Kirsten rat sarcoma viral oncogene homolog, KRAS1, PR310 c-K-ras oncogene, RASK2, RASK_HUMAN, transforming protein p21, and v-Ki-ras2 Kirsten rat sarcoma viral oncogene homolog. The splice variant of KRAS is referred to as K-RAS4A, K-Ras4A, K-ras4A, Kras4A, K-RAS4A. In addition to KRAS, other RAS isoforms in humans include HAS and NRAS.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiologic effect. The effect can be therapeutic in terms of partial or complete cure of a disease, condition, symptom or adverse effect attributed to the disease, disorder, or condition. The term "treatment" as used herein can include any treatment of a disorder of uncontrolled cellular proliferation, such as a cancer, in a subject, particularly a human and can include any one or more of the following: (a) inhibiting the disease, i.e., arresting its development; and (b) relieving the disease, i.e., mitigating or ameliorating the disease and/or its symptoms or conditions. Those in need of treatment (subjects in need thereof) can include those already with the disorder. As used herein, the term "treating", can include inhibiting the disease, disorder or condition, e.g., impeding its progress; and relieving the disease, disorder, or condition, e.g., causing regression of the disease, disorder, and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic.

The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkanediyl", as used herein, unless otherwise indicated, means bivalent straight and branched chained saturated hydrocarbon radicals having carbon atoms. For example, "C1-C6 alkanediyl" would refer to bivalent straight and branched chained saturated hydrocarbon radicals having 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2-$ or $-OA^1-(OA^2)_a-OA^3$, where "a" is an integer of from 1 to 200 and $A^1$, $A^2$, and $A^3$ are alkyl and/or cycloalkyl groups.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $-NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "alkylamino" as used herein is represented by the formula $-NH(\text{-alkyl})$ or $-N(\text{-alkyl})_2$ where alkyl is a described herein, and in the specific instance of $-N(\text{-alkyl})_2$, each alkyl can be independently varied. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "carboxylic acid" as used herein is represented by the formula $-C(O)OH$.

The term "ester" as used herein is represented by the formula $-OC(O)A^1$ or $-C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C-A^2-C(O)O)_a-$ or $-(A^1O(O)C-A^2-OC(O))_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The terms "halo," "halogen" or "halide," as used herein can be used interchangeably and refer to F, Cl, Br, or I.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted.

Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "thiol" as used herein is represented by the formula —SH.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

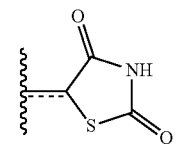

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

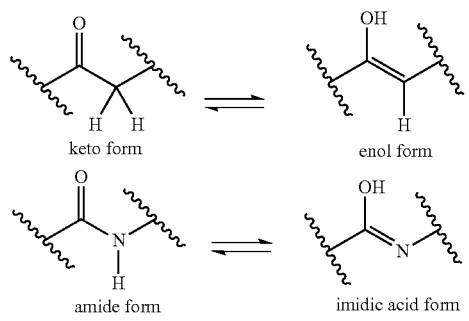

keto form     enol form amide form     imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

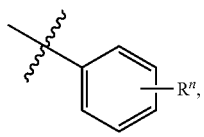

which is understood to be equivalent to a formula:

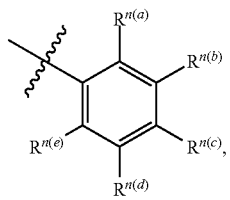

wherein n is typically an integer. That is, $R^n$ is understood to represent five independent substituents, $R^{n(a)}$, $R^{n(b)}$, $R^{n(c)}$, $R^{n(d)}$ and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

It is understood, that unless otherwise specified, temperatures referred to herein are based on atmospheric pressure (i.e. one atmosphere).

Described herein are substituted 7-(piperazin-1-yl)pyrazolo[1,5-a]pyrimidine analogs that have therapeutic or clinical utility. Also described herein are methods of administering the disclosed compounds to a subject in need thereof. In some aspects, the subject can have a disorder of uncontrolled cellular proliferation, such as a cancer. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds.

In various aspects, the present disclosure provides methods of treatment comprising administration of a therapeutically effective amount of a disclosed compound or pharmaceutical composition as disclosed herein above to a subject in need thereof. The disclosed compound used in the methods described herein or as a compound in a disclosed pharmaceutical composition is a substituted pyrazolo[1,5-a]pyrimidin-7-yl)piperazine analog.

In some aspects, the disclosed substituted pyrazolo[1,5-a]pyrimidin-7-yl)piperazine analogs have a structure represented by a formula:

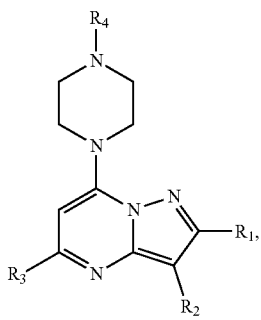

wherein $R_1$ is C1-C6 alkyl; wherein each of $R_2$ and $R_3$ is independently a C1-C8 alkyl, cycloalkyl, heterocycloalkyl, aryl, or heteroaryl; and wherein $R_4$ is —(C1-C6 alkyl), —(C1-C6 alkanediyl)-SF$_5$, —(C1-C6 alkanediyl)-OH, —(C1-C6 alkanediyl)-SH, —(C1-C6 alkanediyl)-NH$_2$, —(C1-C7 haloalkyl), —C1-C7 hydroxyalkyl, —(C1-C6 alkyl)(C=O)R$_5$; wherein $R_5$ is hydroxy, amino, —O(C1-C6 alkyl), —O(C1-C6 haloalkyl), —NH(C1-C6 alkyl), or —N(C1-C6 alkyl)$_2$, or a pharmaceutically acceptable salt thereof, and a pharmaceutically acceptable carrier.

In some aspects, the disclosed substituted pyrazolo[1,5-a]pyrimidin-7-yl)piperazine analog has a structure represented by a formula:

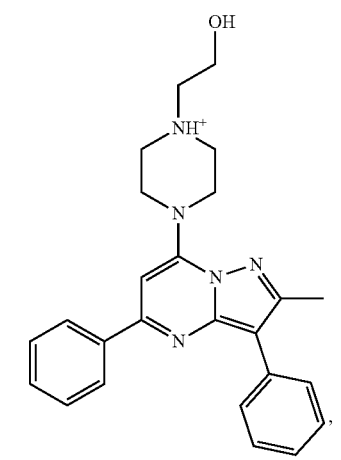

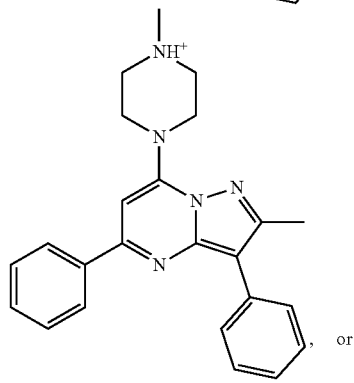

, or

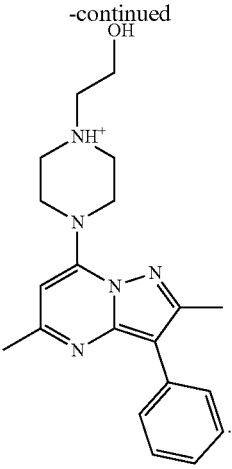

The foregoing compounds can be referred to herein throughout as Compound 11, Compound 12, and Compound 13.

In a further aspect, the disclosed substituted pyrazolo[1,5-a]pyrimidin-7-yl)piperazine analog has a structure represented by a formula:

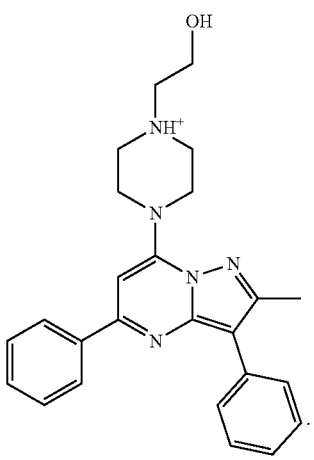

The disclosed substituted pyrazolo[1,5-a]pyrimidin-7-yl)piperazine analogs can be prepared by the skilled artisan, or in some instances, can be commercially obtained from various vendors. For example, the compound shown immediately above (and other related analogues) is commercially available from MolPort (Cat. #MolPort-002-649-559; MolPort, Riga, Latvia). Alternatively, methods suitable for use in preparing the disclosed compounds, or as adapted by the skilled artisan, have been described in the literature (e.g., see Agarwal, R. and Kumar, S. Beilstein J. Org. Chem. 2018, 14, 203-242; Damont, A., et al., J. Med. Chem. 2015, 58, 7449-7464; and Ismail, N. S. M. et al., Fut. J. Pharm. Sci. 2 (2016) 60e70).

Methods of Treating a Disease or Disorder

In various aspects, the present disclosure provides methods of treatment comprising administration of a therapeutically effective amount of a disclosed compound or pharmaceutical composition as disclosed herein above to a subject in need thereof.

In a further aspect, the present disclosure provides methods of treatment comprising administration of a therapeutically effective amount of a disclosed compound or pharmaceutical composition as disclosed herein above to a subject in need thereof. In particular, the disclosed compounds and disclosed pharmaceutical compositions can be used in methods of treating a disease or disorder that are associated with increased, aberrant, or dysfunctional levels of KRAS activity in a cell, tissue, or organism. That is, the disclosed compounds and disclosed pharmaceutical compositions can be used to inhibit KRAS activity in a cell, tissue or organism to provide a clinical or therapeutic benefit to a subject which has been determined to or been diagnosed to have with increased, aberrant, or dysfunctional levels of KRAS activity.

In some aspects of the disclosed methods, the subject has been diagnosed with a need for treatment prior to the administering step. In some aspects of the disclosed method, the subject has been diagnosed with a disorder treatable by inhibition of KRAS and/or a need for inhibition of KRAS prior to the administering step. In some aspects of the disclosed method, the subject has been diagnosed with a cancer, a disorder associated with uncontrolled cellular proliferation prior to the administering step. In some aspects of the disclosed methods, the subject has been identified with a need for treatment prior to the administering step.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In a further aspect, the present disclosure pertains to a methods for treating a disorder of uncontrolled cellular proliferation, such as a cancer, via inhibition of KRAS by administering to a subject in need of such treatment an effective amount of at least one disclosed compound or at least one disclosed pharmaceutical composition.

In a further aspect, the present disclosure pertains to a methods for treating a disorder of uncontrolled cellular proliferation, such as a cancer, via inhibition of KRAS by administering to a subject in need of such treatment an effective amount of at least one disclosed compound or at least one disclosed pharmaceutical composition in combination (simultaneously or sequentially) with at least one other anti-cancer agent.

Cancers and malignant neoplastic that can be treated by the disclosed pharmaceutical compositions include, but are not limited, to prostate, ovarian and brain cancer. Carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

In further aspects, the disclosed pharmaceutical compositions can be used in the chemoprevention of cancer. Chemoprevention is understood to be a clinical intervention to inhibit the development of invasive cancer by either blocking the initiating mutagenic event or by blocking the progression of pre-malignant cells that have already suffered an insult or inhibiting tumor relapse. Accordingly, the disclosed compounds and disclosed pharmaceutical compositions can be used in inhibiting tumor angiogenesis and metastasis.

In a further aspect, the disclosed pharmaceutical compositions can be used in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; BTK inhibitors, SYK inhibitors, ITK inhibitors, PI3-kinase inhibitors, FLT3 inhibitors, EGF inhibitors; PAK inhibitors, VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well. These agents can be used in combination with differentiation agents such as ATRA, EZH2 inhibitors, DNMT inhibitors, corticosteroids, IDH1 inhibitors, IDH2 inhibitors, and Vitamin C. These agents can be used in combination with small molecules that enhance DNA damage killing in cancer cells including PARP inhibitors, MDM2 inhibitors, NAMPT inhibitors, and HSP90 inhibitors. These agents can be used in combination with antibodies that target cell surface molecules on immune or cancer cells including but not limited to CD33, CD37, CD19, CD20, CD3, CD123, CD70, BAFFR, CD4, CD8, CD56, and CD38. These agents can be used in combination with antibodies or peptides which neutralize cytokines including, but not limited to IL1Beta, IL6, IL10, IL21, TNFA, TNFB, GIFN. These agents can be used in combination with cellular CAR-T cells to diminish cellular proliferation in the setting of significant cytokine release syndrome and neurotoxicity. These agents can be used to diminish T-cell proliferation, cytokine production, and neurotoxicity in combination with bi-specific antibodies or peptide molecules that target in a dual manner T-cells and immune/tumor cell antigens such as, but not limited to CD19, CD20 CD33, CD123, CD38, and CD37. These agents can be used to diminish T-cell proliferation and tissue damage caused by immune check point inhibitor antibodies to targets such as, but not limited to PD1, PDL1, CTLA4, and LAG3.

In a further aspect, the disclosed pharmaceutical compositions can be used in combination with a chemotherapeutic agent.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33:183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such as clodronate (for example, BONEFOSO® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN®) combined with 5-FU and leucovovin.

Herein, chemotherapeutic agents include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

Herein, a "taxoid" is a chemotherapeutic agent that functions to inhibit microtubule depolymerization. Examples include paclitaxel (TAXOL®), albumin-engineered nanoparticle formulation of paclitaxel (ABRAXANE™), and docetaxel (TAXOTERE®). The preferred taxoid is paclitaxel.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, lmclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al., Eur. J. Cancer, 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem., 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA J) 4-(3'-Chloro-4'-fluoroanilino)-7-methoxy-6-(3-morpholino propoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-qu inolinyl]-4-(dimethylamino)-2-butenamide) (Wyeth); AG1478 (Sugen); AG1571 (SU 5271; Sugen); dual EGFR/ HER2 tyrosine kinase inhibitors such as lapatinib (GW 572016 or N-[3-chloro-4-[(3fluorophenyl)methoxy]phenyl] 6[5[[[2methylsulfonyl)ethyl]amino]methyl]-2-furanyl]-4-quinazolinamine; Glaxo-SmithKline).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVAC J) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as C1-1033 (Pfizer); Affinitac (ISIS 3521; Isis/Lilly); Imatinib mesylate (Gleevac; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanamid); WO98/43960 (American Cyanamid); WO97/38983 (Warner Lambert); WO99/06378 (Warner Lambert); WO99/06396 (Warner Lambert); WO96/ 30347 (Pfizer, Inc); WO96/33978 (Zeneca); WO96/3397 (Zeneca); and WO96/33980 (Zeneca).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO);

osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

In a further aspect, the disclosed pharmaceutical compositions can be used in combination with actinomycin D, capecitabine, carboplatin, cisplatin, colchicine, daunorubicin, docetaxel, doxorubicin, epirubicin, etoposide, 5-fluorouracil, gemcitabine, melphalan, methotrexate, mitomycin C, mitoxantrone, paclitaxel, thalidomide, topotecan, vinblastine, and vincristine In a further aspect, the disclosed pharmaceutical compositions can be used in combination with antibody against VEGF, Avastin®, an antibody against CD20, rituximab, bortezomib In a further aspect, the disclosed pharmaceutical compositions can be used in combination with a targeted therapy including, but not limited to, bevacizumab, gefitinib, erlotinib, cetuximab, and panitumumab.

In a further aspect, the disclosed pharmaceutical compositions can be used in combination with a chemotherapeutic agent selected from alkylating agents, antimetabolites, platinating agents, topoisomerase inhibitors, tubulin agents, signalling inhibitors (e.g., kinase inhibitors), and other chemotherapeutic agents.

In a further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide.

In a further aspect, the mTor inhibitor agent is selected from one or more of the group consisting of everolimus, siroliumus, and temsirolimus.

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-06-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of inhibition of KRAS activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for inhibiting KRAS activity (e.g., treatment of one or more disorders of uncontrolled cellular proliferation, such as a cancer, associated with a KRAS dysfunction) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a KRAS inhibitor. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Kits.

In various aspects, the present disclosure pertains to kits comprising a therapeutically effective amount of at least one disclosed compound or a disclosed pharmaceutical composition; and optionally, at least one agent known to treat a cancer; and instructions for treating a cancer.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present disclosure also features such kits further containing instructions for use.

In a further aspect, the present disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Research Tools.

The disclosed compounds and pharmaceutical compositions have activity as inhibitors of KRAS activity or inhibitors of cell proliferation. As such, the disclosed compounds are also useful as research tools. Accordingly, one aspect of the present disclosure relates to a method of using a compound of the disclosure as a research tool, the method comprising conducting a biological assay using a compound of the disclosure. Compounds of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a compound of the disclosure to provide a second assay value; wherein step (a) is conducted either before, after or concurrently with step (b); and (c) comparing the first assay value from step (a) with the second assay value from step (b). Exemplary biological assays include an in vitro KRAS GDP/GTP exchange assay or in a cell culture-based assay measuring cell proliferation. Methods suitable for carrying out such assays are described herein. Still another aspect of the disclosure relates to a method of studying a biological system, e.g., a model animal for a clinical condition, or biological sample comprising a KRAS protein, the method comprising: (a) contacting the biological system or sample with a compound of the disclosure; and (b) determining the effects caused by the compound on the biological system or sample.

REFERENCES

References are cited herein throughout using the format of reference number(s) enclosed by parentheses corresponding to one or more of the following numbered references. For example, citation of references numbers 1 and 2 immediately herein below would be indicated in the disclosure as (1, 2).

1. Cox A D & Der C J (2010) Ras history: The saga continues. Small GTPases 1(1):2-27.
2. Prior I A, Lewis P D, & Mattos C (2012) A comprehensive survey of Ras mutations in cancer. Cancer Res 72(10): 2457-2467.
3. Hancock J F, Magee A I, Childs J E, & Marshall C J (1989) All Ras proteins are polyisoprenylated but only some are palmitoylated. Cell 57(7):1167-1177.
4. Vetter I R & Wttinghofer A (2001) Signal transduction—The guanine nucleotide-binding switch in three dimensions. Science 294(5545):1299-1304.
5. Prakash P & Gorfe A A (2014) Overview of simulation studies on the enzymatic activity and conformational dynamics of the GTPase Ras. Mol Simul 40(10-11):839-847.
6. Prakash P & Gorfe A A (2013) Lessons from computer simulations of Ras proteins in solution and in membrane. Biochim Biophys Acta 1830(11):5211-5218.
7. McCormick F & Wttinghofer A (1996) Interactions between Ras proteins and their effectors. Curr Opin Biotech 7(4):449-456.
8. Schubbert S, Shannon K, & Bollag G (2007) Hyperactive Ras in developmental disorders and cancer. Nat Rev. Cancer 7(4):295-308.
9. Hancock J F (2003) Ras proteins: different signals from different locations. Nat Rev. Mol Cell Biol 4(5):373-384.
10. Stephen A G, Esposito D, Bagni R K, & McCormick F (2014) Dragging Ras back in the ring. Cancer Cell 25(3): 272-281.
11. Gorfe A A (2010) Mechanisms of allostery and membrane attachment in Ras GTPases: implications for anti-cancer drug discovery. Curr Med Chem 17(1):1-9.
12. Singh H, Longo D L, & Chabner B A (2015) Improving prospects for targeting RAS. J Clin Onco 33(31):3650-3659.

13. Rojas A M, Fuentes G, Rausell A, & Valencia A (2012) The Ras protein superfamily: evolutionary tree and role of conserved amino acids. J Cell Biol 196(2):189-201.
14. Hauschild A, et al. (2012) Dabrafenib in BRAF-mutated metastatic melanoma: a multicentre, open-label, phase 3 randomised controlled trial. The Lancet 380(9839):358-365.
15. Zimmermann G, et al. (2013) Small molecule inhibition of the KRAS-PDEdelta interaction impairs oncogenic KRAS signalling. Nature 497(7451):638-642.
16. van der Hoeven D, et al. (2013) Fendiline inhibits K-Ras plasma membrane localization and blocks K-Ras signal transmission. Mol Cell Biol 33(2):237-251.
17. Cho K J, et al. (2012) Staurosporines disrupt phosphatidylserine trafficking and mislocalize Ras proteins. J Biol Chem 287(52):43573-43584.
18. Rudolph J & Stokoe D (2014) Selective inhibition of mutant Ras protein through covalent binding. Angew Chem Int Ed. 53(15):3777-3779.
19. Grant B J, et al. (2011) Novel Allosteric Sites on Ras for Lead Generation. PloS one 6(10).
20. Grant B J, Gorfe A A, & McCammon J A (2010) Large conformational changes in proteins: signaling and other functions. Curr Opin Struct Biol 20(2):142-147.
21. Spiegel J, Cromm P M, Zimmermann G, Grossmann T N, & Waldmann H (2014) Small-molecule modulation of Ras signaling. Nat Chem Biol 10(8):613-622.
22. Hocker H J, et al. (2013) Andrographolide derivatives inhibit guanine nucleotide exchange and abrogate oncogenic Ras function. Proc Natl Acad Sci USA 110(25): 10201-10206.
23. Maurer T, et al. (2012) Small-molecule ligands bind to a distinct pocket in Ras and inhibit SOS-mediated nucleotide exchange activity. Proc Natl Acad Sci USA 109(14): 5299-5304.
24. Sun Q, et al. (2012) Discovery of Small Molecules that Bind to K-Ras and Inhibit Sos-Mediated Activation. Angew Chem Int Ed. 51(25):6140-6143.
25. Shima F, et al. (2013) In silico discovery of small-molecule Ras inhibitors that display antitumor activity by blocking the Ras-effector interaction. Proc Natl Acad Sci USA 110(20):8182-8187.
26. Xie C, et al. (2017) Identification of a new potent inhibitor targeting KRAS in non-small cell lung cancer Cells. Front Pharm 8:823.
27. Trinh T B, Upadhyaya P, Qian Z, & Pei D (2016) Discovery of a direct Ras inhibitor by screening a combinatorial library of cell-permeable bicyclic peptides. ACS Comb Sci 18(1):75-85.
28. Upadhyaya P, Qian Z, Habir N A, & Pei D (2014) Direct Ras inhibitors identified from a structurally rigidified bicyclic peptide library. Tetrahedron 70(42):7714-7720.
29. Spencer-Smith R, et al. (2017) Inhibition of RAS function through targeting an allosteric regulatory site. Nat Chem Biol 13(1):62-68.
30. Xiong Y, et al. (2017) Covalent guanosine mimetic inhibitors of G12C KRAS. ACS Med Chem Lett 8(1):61-66.
31. Ostrem J M, Peters U, Sos M L, Wells J A, & Shokat K M (2013) K-Ras(G12C) inhibitors allosterically control GTP affinity and effector interactions. Nature 503(7477): 548-551.
32. McCarthy M, Prakash P, & Gorfe A A (2016) Computational allosteric ligand binding site identification on Ras proteins. Acta Biochim Biophys Sin 48(1):3-10.
33. Prakash P, Hancock J F, & Gorfe A A (2015) Binding hotspots on K-ras: consensus ligand binding sites and other reactive regions from probe-based molecular dynamics analysis. Proteins 83(5):898-909.
34. Prakash P, Sayyed-Ahmad A, & Gorfe A A (2015) pMD-membrane: A method for ligand binding site Identification in membrane-bound proteins. PLoS Comput Biol 11(10):e1004469.
35. Neal S E, Eccleston J F, Hall A, & Webb M R (1988) Kinetic Analysis of the hydrolysis of GTP by p21 N-Ras. J Bio Chem 263(36):19717-19722.
36. Hunter J C, et al. (2015) Biochemical and structural analysis of common cancer-associated KRAS mutations. Mol Cancer Res 13(9):1325-1335.
37. Sayyed-Ahmad A, Prakash P, & Gorfe A A (2017) Distinct dynamics and interaction patterns in H- and K-Ras oncogenic P-loop mutants. Proteins 85(9):1618-1632.
38. Irwin J J, Sterling T, Mysinger M M, Bolstad E S, & Coleman R G (2012) ZINC: A free tool to discover chemistry for biology. J Chem Inf Model 52(7):1757-1768.
39. Morris G M, et al. (1998) Automated docking using a Lamarckian genetic algorithm and an empirical binding free energy function. J Comput Chem 19(14):1639-1662.
40. Jiang X, Kumar K, Hu X, Wallqvist A, & Reifman J (2008) DOVIS 2.0: an efficient and easy to use parallel virtual screening tool based on AutoDock 4.0. Chem Cent J 2:18.
41. Trott O & Olson A J (2010) AutoDock Vina: Improving the speed and accuracy of docking with a new scoring function, efficient optimization, and multithreading. J Comput Chem31(2):455-461.
42. Durrant J D & McCammon J A (2011) BINANA: a novel algorithm for ligand-binding characterization. J Mol Graph Model 29(6):888-893.
43. Plowman S J, Ariotti N, Goodall A, Parton R G, & Hancock J F (2008) Electrostatic interactions positively regulate K-Ras nanocluster formation and function. Mol Cell Biol 28(13):4377-4385.
44. Clayton A H, Hanley Q S, & Verveer P J (2004) Graphical representation and multicomponent analysis of single-frequency fluorescence lifetime imaging microscopy data. J Microsc 213(Pt 1):1-5.
45. Verveer P J & Bastiaens P I H (2003) Evaluation of global analysis algorithms for single frequency fluorescence lifetime imaging microscopy data. J microsc 209 (1):1-7.
46. Esposito A, Gerritsen H C, & Wouters F S (2005) Fluorescence lifetime heterogeneity resolution in the frequency domain by lifetime moments analysis. Biophys J 89(6):4286-4299.
47. Burns M C, et al. (2014) Approach for targeting Ras with small molecules that activate SOS-mediated nucleotide exchange. Proc Natl Acad Sci USA 111(9):3401-3406.
48. Gremer L, et al. (2011) Germline KRAS mutations cause aberrant biochemical and physical properties leading to developmental disorders. Hum Mutat 32(1):33-43.
49. Nakhaeizadeh H, Amin E, Nakhaei-Rad S, Dvorsky R, & Ahmadian M R (2016) The RAS-effector interface: Isoform-specific differences in the effector binding regions. PloS one 11(12):e0167145.
50. Poulikakos P I, Zhang C, Bollag G, Shokat K M, & Rosen N (2010) RAF inhibitors transactivate RAF dimers and ERK signalling in cells with wild-type BRAF. Nature 464(7287):427-430.
51. Boriack-Sjodin P A, Margarit S M, Bar-Sagi D, & Kuriyan J (1998) The structural basis of the activation of Ras by Sos. Nature 394(6691):337-343.

53

52. Hall B E, Bar-Sagi D, & Nassar N (2002) The structural basis for the transition from Ras-GTP to Ras-GDP. Proc Natl Acad Sci USA 99(19):12138-12142.

Aspects

The following listing of exemplary aspects supports and is supported by the disclosure provided herein:

Aspect 1. A pharmaceutical composition comprising a compound having a structure represented by a formula:

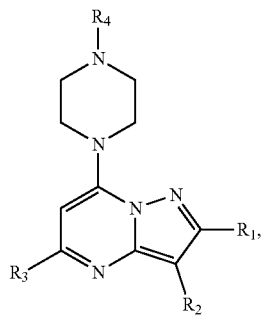

wherein $R_1$ is C1-C6 alkyl; wherein each of $R_2$ and $R_3$ is independently a C1-C8 alkyl, cycloalkyl, heterocycloalkyl, aryl, or heteroaryl; and wherein $R_4$ is —(C1-C6 alkyl), —(C1-C6 alkanediyl)-SF$_5$, —(C1-C6 alkanediyl)-OH, —(C1-C6 alkanediyl)-SH, —(C1-C6 alkanediyl)-NH$_2$, —(C1-C7 haloalkyl), —C1-C7 hydroxyalkyl, —(C1-C6 alkyl)(C=O)R$_5$; wherein R$_5$ is hydroxy, amino, —O(C1-C6 alkyl), —O(C1-C6 haloalkyl), —NH(C1-C6 alkyl), or —N(C1-C6 alkyl)$_2$, or a pharmaceutically acceptable salt thereof, and a pharmaceutically acceptable carrier.

Aspect 2. The pharmaceutical composition of Aspect 1, wherein $R_1$ is methyl, ethyl, propyl or isopropyl.

Aspect 3. The pharmaceutical composition of Aspect 1, wherein $R_1$ is methyl.

Aspect 4. The pharmaceutical composition of any one of 1-3, wherein each of $R_2$ and $R_3$ is independently a C1-C8 alkyl, cycloalkyl, heterocycloalkyl, or aryl.

Aspect 5. The pharmaceutical composition of 3, wherein each of $R_2$ and $R_3$ is independently a methyl, ethyl, propyl, isopropyl, n-butyl, tert-butyl, sec-butyl, isobutyl, neopentyl, isopentyl, sec-pentyl, tert-pentyl, 3,3-dimethylbutan-2-yl, 2,3-dimethylbutan-2-yl, cyclopropyl, cyclopentyl, cyclohexyl, cycloheptyl, cyclooctyl, phenyl, benzyl, or naphthyl.

Aspect 6. The pharmaceutical composition of 4, wherein $R_2$ is isopropyl, n-butyl, tert-butyl, sec-butyl, isobutyl, neopentyl, isopentyl, sec-pentyl, tert-pentyl, 3,3-dimethylbutan-2-yl, 2,3-dimethylbutan-2-yl, cyclopropyl, cyclopentyl, cyclohexyl, cycloheptyl, cyclooctyl, benzyl, phenyl, naphthyl; and wherein $R_3$ is isopropyl, n-butyl, tert-butyl, sec-butyl, isobutyl, neopentyl, isopentyl, sec-pentyl, tert-pentyl, 3,3-dimethylbutan-2-yl, 2,3-dimethylbutan-2-yl, benzyl, phenyl, or naphthyl.

Aspect 7. The pharmaceutical composition of 3, wherein each of $R_2$ and $R_3$ is independently an aryl.

Aspect 8. The pharmaceutical composition of Aspect 7, wherein each of $R_2$ and $R_3$ is independently phenyl, benzyl, or naphthyl.

Aspect 9. The pharmaceutical composition of Aspect 8, wherein $R_2$ is phenyl; and wherein $R_3$ is phenyl, benzyl, or naphthyl.

54

Aspect 10. The pharmaceutical composition of Aspect 8, wherein $R_2$ is phenyl, benzyl, or naphthyl; and wherein $R_3$ is phenyl.

Aspect 11. The pharmaceutical composition of Aspect 8, wherein each of $R_2$ and $R_3$ is phenyl.

Aspect 12. The pharmaceutical composition of 3, wherein each of $R_2$ and $R_3$ is independently cycloalkyl or heterocycloalkyl.

Aspect 13. The pharmaceutical composition of Aspect 12, wherein each of $R_2$ and $R_3$ is independently cyclopropyl, cyclopentyl, cyclohexyl, cycloheptyl, cyclooctyl, aziridinyl, oxiranyl, thiiranyl, azetidinyl, oxetanyl, thietanyl, pyrrolidinyl, tetrahydrofuranyl, tetrahydrothiophenyl, piperidinyl, tetrahydro-2H-pyranyl, tetrahydro-2H-thiopyranyl, azepanyl, oxepanyl, thiepanyl, azocanyl, oxocanyl, thiocanyl, imidazolidinyl, pyrazolidinyl, oxazolidinyl, piperazinyl, tetrahydropyrimidinyl, tetrahydropyridazinyl, oxazinanyl, morpholinyl, diazepanyl, thiomorpholinyl, pyrrolo[3,4-c] pyrrolyl, Aspect 14. The pharmaceutical composition of any one of 1-Aspect 13, wherein $R_4$ is methyl, ethyl, propyl, isopropyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$(C=O)OCH$_3$, —CH$_2$(C=O)OCH$_2$CH$_3$., —CH$_2$NH$_2$, —(CH$_2$)$_2$NH$_2$, or —(CH$_2$)$_2$NH$_2$.

Aspect 15. The pharmaceutical composition of 9, wherein $R_4$ is —CH$_2$F, —CH$_2$Cl, —CH$_2$CH$_2$F, —CH$_2$CH$_2$Cl, —CH$_2$OH, —(CH$_2$)$_2$OH, —CH$_2$NH$_2$, or —(CH$_2$)$_2$NH$_2$.

Aspect 16. The pharmaceutical composition of 9, wherein $R_4$ is —CH$_2$OH or —(CH$_2$)$_2$OH.

Aspect 17. The pharmaceutical composition of Aspect 1, wherein the compound is present as:

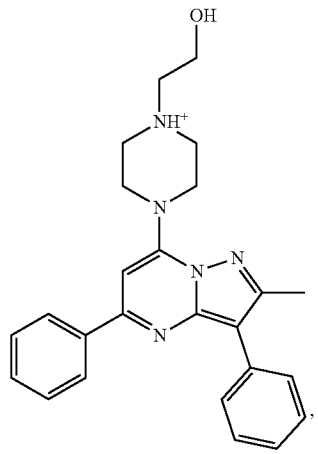 [SMILES: Cc1nn2c(N3CC[NH+](CCO)CC3)cc(-c3ccccc3)nc2c1-c1ccccc1]

,

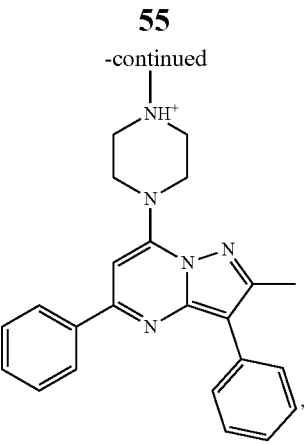

or combinations thereof.

Aspect 18. The pharmaceutical composition of 8, wherein the compound is present as:

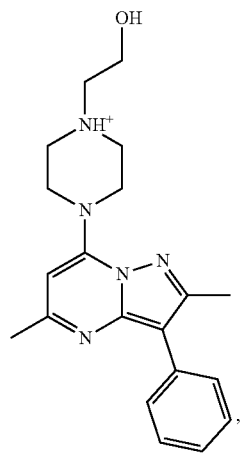
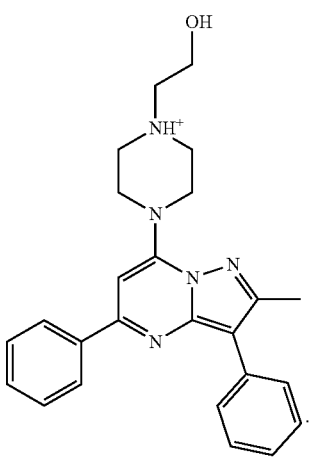 [SMILES: Cc1nn2c(N3CC[NH+](CCO)CC3)cc(-c3ccccc3)nc2c1-c1ccccc1]

Aspect 19. The pharmaceutical composition of any one of 1-Aspect 18, wherein the compound is a pharmaceutically acceptable salt.

Aspect 20. The pharmaceutical composition of 9, wherein the pharmaceutically acceptable salt is a compound having a structure represented by the formula:

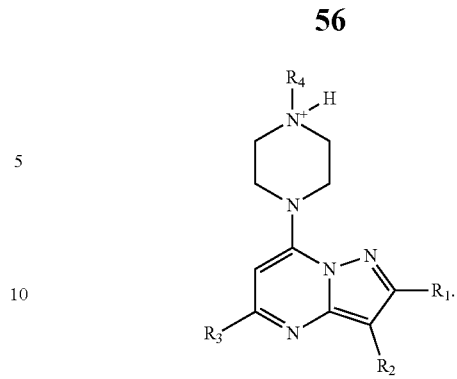

Aspect 21. The pharmaceutical composition of any one of 1-11, further a therapeutically effective amount of at least one agent known to treat a cancer.

Aspect 22. The pharmaceutical composition of Aspect 21, wherein the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, and vasostatin.

Aspect 23. The pharmaceutical composition of Aspect 21, wherein the at least one agent is a DNA methyltransferase inhibitor, an HDAC-inhibitor, a glucocorticoid, an mTOR inhibitor, a cytotoxic agent, or combinations thereof.

Aspect 24. The pharmaceutical composition of Aspect 23, wherein the DNA methyltransferase inhibitor is 5-aza-2'-deoxycytidine, 5-azacytidine, zebularin, epigallocatechin-3-gallate, procaine, or combinations thereof.

Aspect 25. The pharmaceutical composition of Aspect 23, wherein the HDAC-inhibitor is vorinostat, entinostat, panbinostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, or combinations thereof.

Aspect 26. The pharmaceutical composition of Aspect 23, wherein the glucocorticoid is dexamethasone, prednisolone, methylprednisolone, betamethasone, triamicinolone, fludrocortisone, beclomethasone, or combinations thereof.

Aspect 27. The pharmaceutical composition of Aspect 23, wherein the mTor inhibitor is BEZ235, everolimus, temsirolimus, rapamycin, AZD8055, or combinations thereof.

Aspect 28. The pharmaceutical composition of Aspect 23, wherein the cytotoxic agent is an alkylating agent, an antimetabolite agent, an antineoplastic antibiotic agent, a mitotic inhibitor agent, a mTor inhibitor agent or other chemotherapeutic agent.

Aspect 29. The pharmaceutical composition of Aspect 28, wherein the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

Aspect 30. The pharmaceutical composition of Aspect 28, wherein the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

Aspect 31. The pharmaceutical composition of Aspect 28, wherein the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

Aspect 32. The pharmaceutical composition of Aspect 28, wherein the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

Aspect 33. The pharmaceutical composition of Aspect 28, wherein the mTor inhibitor is everolimus, sirolimus, temsirolimus, or combinations thereof.

Aspect 34. The pharmaceutical composition of Aspect 28, wherein the other chemotherapeutic agent is an anthracycline, cytarabine, a purine analog, sorafenib, gemtuzumab ozogamicin, rituximab, or combinations thereof.

Aspect 35. The pharmaceutical composition of Aspect 34, wherein the anthracycline is daunorubicin, idarubicin, or combinations thereof.

Aspect 36. The pharmaceutical composition of Aspect 34, wherein the purine analog is cladribine, fludarabine, clofarabine, or combinations thereof.

Aspect 37. A method for the treatment of a disease or disorder in a mammal comprising the step of administering to the mammal a pharmaceutical composition of any one of 1-Aspect 36.

Aspect 38. The method of 12, wherein the mammal is a human.

Aspect 39. The method of 12, wherein the mammal has been diagnosed with a need for treatment of the disorder prior to the administering step.

Aspect 40. The method of Aspect 39, wherein the disorder or disease is associated with abnormal, increased, or aberrant dihydroorotate dehydrogenase (DHODH) activity.

Aspect 41. The method of 13, wherein the disorder or disease can be treated by inhibition of dihydroorotate dehydrogenase (DHODH) activity.

Aspect 42. The method of Aspect 39, wherein the disorder or disease is associated with abnormal, increased, or aberrant serine/threonine-protein kinase B-Raf activity.

Aspect 43. The method of Aspect 42, wherein the disorder or disease can be treated by inhibition of serine/threonine-protein kinase B-Raf activity.

Aspect 44. The method of any one of 12-Aspect 43, further comprising the step of identifying a mammal in need of treatment of the disorder or disease.

Aspect 45. The method of Aspect 44, wherein the disorder or disease is associated with abnormal, increased, or aberrant dihydroorotate dehydrogenase (DHODH) activity.

Aspect 46. The method of Aspect 45, wherein the disorder or disease can be treated by inhibition of dihydroorotate dehydrogenase (DHODH) activity.

Aspect 47. The method of Aspect 44, wherein the disorder or disease is associated with abnormal, increased, or aberrant serine/threonine-protein kinase B-Raf activity.

Aspect 48. The method of Aspect 47, wherein the disorder or disease can be treated by inhibition of serine/threonine-protein kinase B-Raf activity.

Aspect 49. The method of any one of 12-Aspect 46, wherein the disorder is a cancer.

Aspect 50. The method of Aspect 49, wherein the cancer is selected from breast cancer, renal cancer, gastric cancer, colorectal cancer, ovarian cancer, prostate cancer, pancreatic cancer, brain cancer, genitourinary tract cancer, lymphatic system cancer, stomach cancer, larynx cancer, lung cancer, pancreatic cancer, breast cancer, and malignant melanoma.

Aspect 51. The method of Aspect 49, wherein the cancer is a hematological cancer.

Aspect 52. The method of 19, wherein the hematological cancer is leukemia, lymphoma, myeloma, myelodysplastic syndrome, or myeloproliferative neoplasm.

Aspect 53. The method of 20, wherein the hematological cancer is chronic myeloid leukemia (CML), acute myeloid leukemia (AML), chronic lymphoid leukemia (CLL), acute lymphoid leukemia (ALL), hairy cell leukemia, chronic myelomonocytic leukemia (CMML), juvenile myelomonocyte leukemia (JMML), large granular lymphocytic leukemia (LGL), acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, Hodgkin lymphoma, and non-Hodgkin lymphoma.

Aspect 54. The method of Aspect 53, wherein the hematological cancer is chronic myeloid leukemia (CML) or acute myeloid leukemia (AML).

Aspect 55. The method of any one of 12-Aspect 54, further comprising the step of administering a therapeutically effective amount of at least one agent known to treat a cancer.

Aspect 56. The method of Aspect 55, wherein the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, and vasostatin.

Aspect 57. The method of Aspect 55, wherein the at least one agent is a DNA methyltransferase inhibitor, an HDAC-inhibitor, a glucocorticoid, an mTOR inhibitor, a cytotoxic agent, or combinations thereof.

Aspect 58. The method of Aspect 57, wherein the DNA methyltransferase inhibitor is 5-aza-2'-deoxycytidine, 5-azacytidine, zebularin, epigallocatechin-3-gallate, procaine, or combinations thereof.

Aspect 59. The method of Aspect 57, wherein the HDAC-inhibitor is vorinostat, entinostat, panbinostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, or combinations thereof.

Aspect 60. The method of Aspect 57, wherein the glucocorticoid is dexamethasone, prednisolone, methylprednisolone, betamethasone, triamicinolone, fludrocortisone, beclomethasone, or combinations thereof.

Aspect 61. The method of Aspect 57, wherein the mTor inhibitor is BEZ235, everolimus, temsirolimus, rapamycin, AZD8055, or combinations thereof.

Aspect 62. The method of Aspect 57, wherein the cytotoxic agent is an alkylating agent, an antimetabolite agent, an antineoplastic antibiotic agent, a mitotic inhibitor agent, a mTor inhibitor agent or other chemotherapeutic agent.

Aspect 63. The method of Aspect 62, wherein the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

Aspect 64. The method of Aspect 62, wherein the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

Aspect 65. The method of Aspect 62, wherein the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

Aspect 66. The method of Aspect 62, wherein the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

Aspect 67. The method of Aspect 62, wherein the mTor inhibitor is everolimus, sirolimus, temsirolimus, or combinations thereof.

Aspect 68. The method of Aspect 62, wherein the other chemotherapeutic agent is an anthracycline, cytarabine, a purine analog, sorafenib, gemtuzumab ozogamicin, rituximab, or combinations thereof.

Aspect 69. The method of Aspect 68, wherein the anthracycline is daunorubicin, idarubicin, or combinations thereof.

Aspect 70. The method of Aspect 68, wherein the purine analog is cladribine, fludarabine, clofarabine, or combinations thereof.

Aspect 71. The method of any one of Aspect 55-Aspect 70, wherein the at least one compound and the at least one agent are administered sequentially.

Aspect 72. The method of any one of Aspect 55-Aspect 70, wherein the at least one compound and the at least one agent are administered simultaneously.

Aspect 73. The method of any one of Aspect 55-Aspect 70, wherein the at least one compound and the at least one agent are co-formulated.

Aspect 74. The method of any one of Aspect 55-Aspect 70, wherein the at least one compound and the at least one agent are co-packaged.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Materials and Methods

Molecular dynamics simulation and allosteric pocket analysis. Most oncogenic RAS mutants are constitutively active because their ability to hydrolyze GTP is compromised (35, 36). An inhibitor that selectively targets GTP-bound mutant RAS would therefore be desirable. It has been previously described that there are four potential allosteric ligand-binding sites on KRAS as determined using a range of computational approaches (32-34). Among these, pocket p1 is the best characterized and is well established as a suitable target with many crystal structures of p1-bound ligand-KRAS complexes available in the protein data bank (PDB). In the present disclosure, combined molecular modeling was combined with a range of biophysical and cell assays to discover and characterize a novel class of inhibitors that bind to the p1 pocket with nanomolar (nM) affinity and abrogate signaling by directly inhibiting the interaction of KRAS with effector proteins.

However, there was no high-resolution experimental structure of GTP-bound KRAS ($^{GTP}$KRAS) when the studies described herein were first initiated, and the target pocket p1 (see below) was closed or was too small in the available GDP-bound KRAS ($^{GDP}$KRAS) structures. Accordingly, molecular dynamics (MD) simulation was used to generate an ensemble of $^{GTP}$KRAS structures. The initial structure for the simulation was a GDP-bound KRAS$^{G12D}$ X-ray structure from the PDB (ID 4DSO) (23). After converting GDP to GTP, removing other molecules except crystal waters, adding hydrogen atoms and solvent, minimization and restrained simulation, a 300 ns production run using an identical protocol to that described in a recent report (37) was conducted. The trajectory was analyzed in terms of volume and other features (such as numbers of hydrogen bond donors and acceptors) of the target pocket p1 and the conformation with the most open p1 was selected for virtual screening of ligand libraries.

High throughput virtual screening. Six million compounds from the Drugs Now subset of the ZINC (38) database were docked into pocket p1 of the MD-derived KRAS$^{G12D}$ structure (FIG. 1A). Gasteiger charges and atomic radii were assigned using AutoDock Tools, and a first round of docking was conducted with AutoDock (39) as implemented in the parallelization routine DOVIS (40). The flexible ligand option with 1.0 Å spacing was used, along with a Lamarckian search with 150 generations and 1,000,000 energy evaluations. The top ~4000 compounds with energy score ≤−6.8 kcal/mol were re-screened with VINA v1.1.2 (41) with exhaustiveness set to 12 and energy range to 4. The top 500 hits in each screen were then evaluated in terms of their ability to form close contact, salt bridge, hydrogen bonding, hydrophobic, cation-π, π-π and π-stacking interactions with the protein, using distance and angle cutoffs recommended by Durant et. al. (42). 58 ligands were identified that score well in the majority of these metrics and experimentally tested 11 that are listed in FIG. S1A (see Appendix I, attached hereto).

Cell signaling. The inhibitory potential of compounds was tested in monoclonal Baby Hamster Kidney (BHK) cell lines stably expressing monomeric green fluorescence protein (mGFP)-tagged KRAS$^{G12D}$, K-Ras$^{G12V}$ and HRAS$^{G12V}$. Cells were cultured in Dulbecco's Modified Eagle Medium (DMEM, Hyclone) supplemented with 10% v/v bovine calf serum and incubated with compound or vehicle (DMSO) for 3 h without serum. Cells were then harvested in lysis buffer (50 mM Tris (pH 7.5), 75 mM NaCl, 25 mM NaF, 5 mM MgCl$_2$, 5 mM EGTA, 1 mM dithiothreitol, 100 µM NaVO$_4$, 1% Nonidet P40 plus protease inhibitors) and subjected to Western analysis controlling protein loading by BCA (bicinchoninic acid) assay. Lysates were resolved with Bio-Rad polyacrylamide TGX 10% gel, transferred to polyvinylidene fluoride (PVDF) membrane and immunoblotted using pan-AKT (2920S), GFP (2956S), pAKT$^{S473}$ (4060L), p-cRaf$^{S338}$ (9427S), p-ERKT$^{T202/Y204}$ (4370L), ERK1/2 (4695S) or β-actin antibodies (Cell Signaling Technology). IC$_{50}$ values were calculated with Prism 4-parameter fit.

Pull-down. GFP-RAS with GST-tagged RAS binding domain (RBD) of cRaf$^{ASK}$ (hereafter GST-Raf$^{RBD}$) pulled down to monitor RAS-Raf interaction. To prepare GST-Raf$^{RBD}$ bound to agarose beads, bacteria (BL21) transfected with a previously cloned GEX plasmid were grown in selection media to OD levels of 0.5-1.0 before protein expression was initiated with IPTG (1:1000). After 4 h, the sample was centrifuged at 6000 rpm for 5 min at 4° C., the pellet was re-suspended with PBS containing 5 mM EGTA, 1% Triton X, PIC 1:50 and PMSF 1:100, and cells were lysed with cycles of freezing and thawing. The lysate was sonicated to breakup DNA, and pelleted. The supernatant was incubated with glutathione agarose (Pierce™) beads that bind to GST-Raf$^{RBD}$. For the pull-down experiments, cell lysates from BHK cells expressing GFP-RAS were incubated for 2 h at 4° C. with GST-RBD beads plus DMSO or compound. Then samples were washed with Tris buffer (50 mM Tris, pH7.4, 1 mM EDTA, 1 mM EGTA, 150 mM NaCl, 0.1% Trition X-100 and protease inhibitors) and immunoblotted with anti-GFP (Cell Signaling) and anti-GST (Santa Cruz Biotechnology) antibodies.

Fluorescence lifetime imaging (FLIM)-fluorescence resonance energy transfer (FRET). FLIM-FRET experiments were carried out using a lifetime fluorescence imaging attachment (Lambert Instruments, The Netherlands) on an inverted microscope (43). BHK cells transiently expressing mGFP-tagged KRAS$^{G12D}$ (donor), alone or with mRFP-tagged cRaf$^{WT}$ (acceptor) (using 1:5 ratio), were prepared as indicated in each experiment. The samples were excited using a sinusoidally modulated 3 W 470 nm light-emitting diode at 40 MHz under epi-illumination. Fluorescein was used as a lifetime reference standard. Cells were imaged with a Plan Apo 60X 1.40 oil objective using an appropriate GFP filter set. The phase and modulation were determined from 12 phase settings using the manufacturer's software. Resolution of two lifetimes in the frequency domain was performed using a graphical method (44) mathematically identical to global analysis algorithms (45, 46). The analysis yields the mGFP lifetime of free mGFP donor (τ1), and the mGFP lifetime in donor/acceptor complexes (τ2). FLIM data were averaged on a per-cell basis.

Cell proliferation. Potential effect of the ligands on cancer cell proliferation was tested in three lung cancer cells: SKLU-1, H1975 and H522. Cells were plated at ~1,000 cell per well in a 96-well plate and maintained in full serum media with or without compound at 37° C. for 72 h changing the media with the compound every 24 h. Media with compound was prepared by serial dilution at concentrations indicated. Then cells were washed with PBS and frozen at −80° C. for a minimum of 24 h. Plates were thawed and CyQuant™ dye (in lysis buffer provided in the CyQuant™ cell proliferation assay kit, Invitrogen™) was added, and after a five-minute incubation, fluorescence (excitation: 480 nm emission: 520 nm) was measured with a Tecan Infinite M200 plate reader.

Microscale thermophoresis (MST. Determination of dissociation constants using MST was performed following vendor protocols. Purified KRAS was labeled with the Monolith MT™ Protein Labeling Kit RED-NHS (NanoTemper Tech) through buffer-exchange in the labeling buffer (40 mM HEPES, pH 7.5, 5 mM $MgCl_2$, 500 mM NaCl). The concentration of the eluted protein was adjusted to 2-20 µM, the dye added at a 2-3-fold concentration to a final volume of 200 µL, and the mixture incubated for 30 min at room temperature in the dark. Labeled KRAS was purified using the column provided in the kit. For MST measurements, a 16-point serial dilution of ligand was prepared in an MST assay buffer (40 mM HEPES, pH 7.5, 5 mM $MgCl_2$, 100 mM NaCl; plus 0.05% Tween-20 and 2-4% DMSO), and added to a 100 nM KRAS solution. The solutions were loaded in capillaries and measurements were done at room temperature using 20% LED and 40% MST power. The data were fit in Igor Pro using the Hill equation.

Nucleotide exchange and release assays. Loading of fluorescent-labeled GDP (BODIPY-GDP; BGDP from hereon) to KRAS was conducted following previous reports (23, 47), with minor modifications. Purified KRAS was buffer-exchanged in NAP-5 column (GE Life Sciences) in low $Mg^{2+}$ buffer (25 mM Tris pH 7.5, 50 mM NaCl, and 0.5 mM $MgCl_2$). The eluate was incubated with 10-fold molar excess of BGDP (Life Technologies) in the presence of 5 mM EDTA and 1 mM DTT for 1.5 h at 20° C. in the dark. Then 10 mM $MgCl_2$ was added and the solution was incubated for 30 min at 20° C. Free nucleotide was removed by gel filtration using a PD-10 column (GE Life Sciences) that had been equilibrated with the reaction buffer (25 mM Tris-HCL pH 7.5, 50 mM NaCl, 1 mM $MgCl_2$, and 1 mM DTT). The concentration of $^{BGDP}$KRAS was determined using Bradford assay and a BGDP standard curve. Then the effect of ligands on the intrinsic rate of nucleotide release was monitored using the decrease in fluorescence with time as BGDP dissociates from KRAS in a 100 µL reaction mixture (96-well plate) of 0.5 µM $^{BGDP}$KRAS, 100 µM GTP and varying concentrations of ligand (0 to 25 µM); GTP was added just before measurements. To measure the rate of SOS-mediated nucleotide release, 0.5 µM SOS (residues 564-1049, Cytoskeleton Inc) was added after adding GTP, and fluorescence was immediately read (excitation: 485 nm, emission: 510 nm) using Tecan Infinite M200 plate reader. Intrinsic and SOS-mediated nucleotide exchange rates were monitored with the fluorescence intensity increase of BGTP as it displaces GDP from KRAS. A 100 µL reaction mixture was used containing 0.5 µM each of $^{GDP}$KRAS, BGTP (and SOS) plus varying concentrations of ligand (0 to 25 µM); BGTP was added just before measurements. Experiments were conducted with minimal light and the reaction was monitored for 2 h at room temperature. Fluorescence intensities were normalized at 120 s and the traces were fit with linear or single exponential functions (Igor Pro, Wavemetrics).

Fluorescence polarization. Fluorescence polarization assay was conducted following previous reports (48, 49). KRAS was pre-loaded with the non-hydrolyzable fluorescent GTP analog BODIPY-GTP-γ-S(BGTP-γ-S; Life Technologies) using buffer-exchange in NAP-5 (GE Life Sciences) as described in the previous section. Then 0.5 µM (50 µL) of $^{BGTP-\gamma-S}$KRAS was incubated with an equal volume but varying concentrations (0 to 2.5 µM) of GST-Raf$^{RBD}$ (Raf RBD residues 1-149; Life Technologies) for 30 min in the dark. To determine the effect of ligand on RAS-Raf binding, KRAS was first incubated with a fixed concentration of the ligand for 30 min and then with GST-Raf$^{RBD}$. Fluorescence polarization was measured using PolarStar Optima plate reader (excitation: 485 nm, emission: 520 nm) at room temperature. GST-tag was used to increase the weight of Raf$^{RBD}$ for a greater polarization. The dissociation constant for KRAS-Raf binding was determined using a quadratic ligand binding equation (48).

Results and Discussion

Initial hits from molecular modeling and high-throughput virtual screening. In silico screening was carried out on compounds from the ZINC database (38) targeting pocket p1 on an MD-derived structure of $^{GTP}$KRAS$^{G12D}$. This pocket is located between the functionally critical switches 1 (residues 25-40) and 2 (residues 60-75), and encompasses residues 5-7, 37-39, 50-56, 67 and 70-75 (FIG. 1A). Many of these residues, including residues 37-39 on the effector binding loop and residue 71 on switch 2, participate in interaction with effectors and/or GEFs. Therefore, it was reasoned that a p1-targeted ligand could disrupt either or both of these interactions. However, p1 was fully or partially closed in the available $^{GDP}$KRAS structures including the holo forms, which were generally bound to small (<160 Da) ligands. It was determined that the screening should include a more open conformation in order to dock a wide range of "drug-like" molecules spanning the ~150-500 Da molecular weight common in marketed drugs. In addition, there was no experimental structure of $^{GTP}$KRAS with a suitable resolution. Accordingly, MD simulation was conducted to generate an ensemble of $^{GTP}$KRAS$^{G12D}$ structures with open p1. Analysis of the trajectory yielded 119 and 219 $Å^3$ as the mean and maximum volumes of pocket p1, respectively. A snapshot with the largest p1 volume was used to conduct an initial screen of 6,000,000 compounds, followed by a secondary screen of the top ~4000 (see Methods). Analysis of the top 500 ligands in each screen yielded a consensus prediction of 58 initial hits. Eleven of these were purchased and tested in cells (FIG. S1A; see Appendix I, attached hereto).

Cell signaling assays identify compound 11 as a promising initial hit Western analysis was used to quickly assess the potential impact of the predicted hits on MAPK signaling, a major pathway mediated by KRAS. Specifically, ERK1/2 phosphorylation levels (p-ERK) were monitored in BHK cells stably expressing KRAS$^{G12D}$ treated with vehicle (DMSO), the MEK inhibitor U0125 (U) or compound at four different concentrations (1-100 µM). The results showed that the majority of the predicted hits have no effect while few (e.g. 4) increase rather than decrease p-ERK levels (FIG. S1B; see Appendix I, attached hereto). Compounds 9 and 11 (structures for compounds 1-11 are provided in Appendix I, attached hereto), on the other hand, decreased p-ERK levels at concentrations ≥50 µM and ≤5 µM, respectively. To verify the latter observation, the experiments were repeated in an expanded concentration range starting from 0.1 µM. As in the first screen, compound 11 dose-dependently decreased p-ERK levels, leading to ~50% reduction at 5 µM (FIG. S1C; see Appendix I, attached hereto). However, compound 9 (see Appendix I, attached hereto) increased p-ERK levels at 25 and 38 µM in contrast to the decrease observed at higher concentrations (FIG. S1B; see Appendix I, attached hereto). Although a similar increase and then decrease of KRAS signaling upon increasing ligand concentration has been observed before (47, 50), in the present disclosure, the more potent and monotonously dose-dependent compound 11 was selected for further analysis.

Figure 1B:
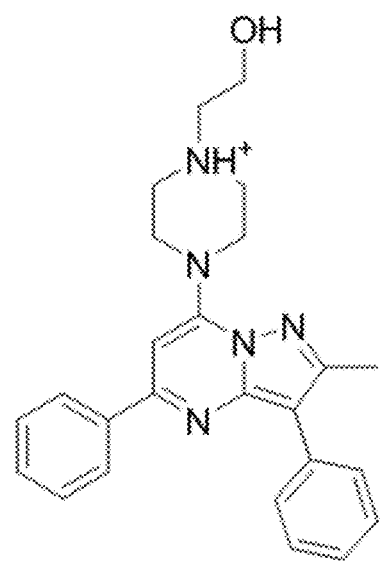
Figure 1C:
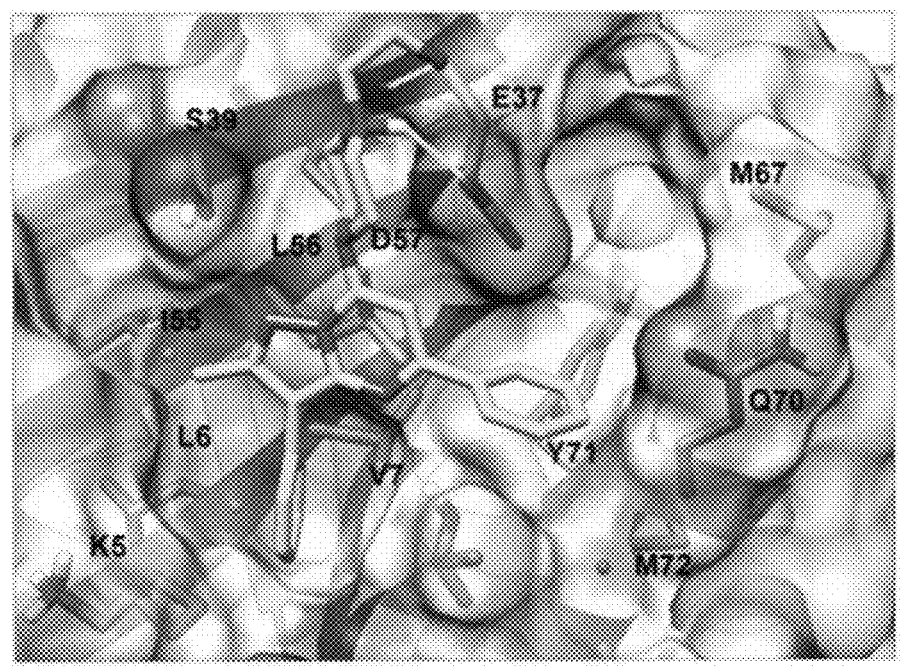
Figure 1D:
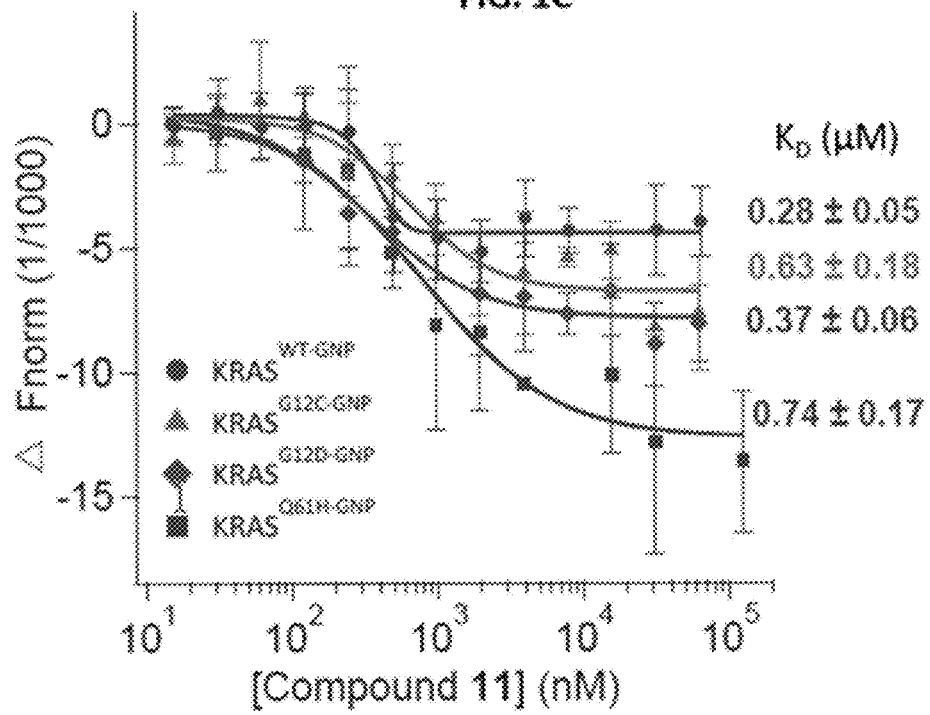

Compound 11 binds to WT and oncogenic KRAS mutants with nanomolar affinity FIGS. 1B and 1C show the chemical structure and the predicted complex of compound 11 with KRAS, showing that the ligand forms multiple favorable interactions with residues in the p1 pocket. FIG. 1D shows that the compound binds to $^{GTP}KRAS^{WT}$ with a $K_D$=~0.3 µM, suggesting a very tight binding rarely seen in primary screens. The compound has a very similar affinity ($K_D$=~0.4-0.7 µM) for oncogenic mutants $KRAS^{G12D}$, $KRAS^{G12C}$ and $KRAS^{Q61H}$ in the GTP state (FIG. 1D). However, no binding was detected to $KRAS^{WT}$ and $KRAS^{G12D}$ in the GDP state or for control Rap1B, a RAS-related small GTPase with homologous structure. Few weak-affinity non-covalent binders that exhibit some selectively toward GDP- or GTP KRAS have been reported (23-25). Surprisingly, compound 11 is the first small molecule to selectively bind to $KRAS^{GTP}$ with nanomolar affinity. In the docked pose (FIG. 1C), the 1-piperazineethanol moiety occupies an electronegative cleft near D54 and D38, and donates hydrogen bonds to the side chain and backbone atoms of E37. The methylated pyrazolopyrimidine core sits in a trench on top of V7 and L56 with the methyl pointing towards I55. The pyrimidine-bound benzene occupies the space between the central beta sheet (β1-β3) and helix 2, making π-stacking interactions with Y71. The pyrazol-attached benzene is buried deep in a tight pocket, stabilized primarily by van der Waals (vdVV) interactions with side chain carbon atoms of V7, L6 and K5; these interactions appear to be crucial for the binding and are common in the majority of the predicted hits listed in FIG. S1A (see Appendix I, attached hereto). Without wishing to be bound by a particular theory, it is believed that in addition to potential ligand-induced conformational changes, the compound's preference for $KRAS^{GTP}$ can be explained by the conformational differences of these residues in $RAS^{GTP}$ versus $RAS_{GDP}$(4).

Figure 2A:
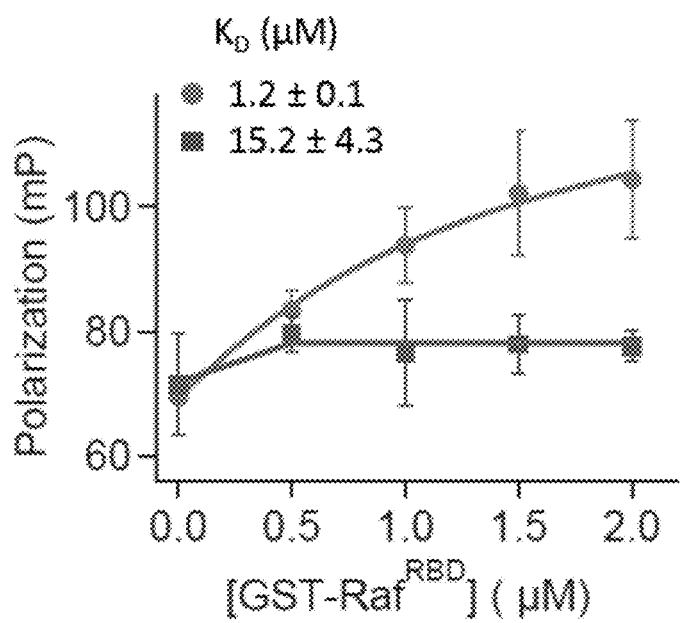
FIGS. 2A-2C show representative data pertaining to the disruption of KRAS-Raf interaction by disclosed compound 11.
Figure 2B:
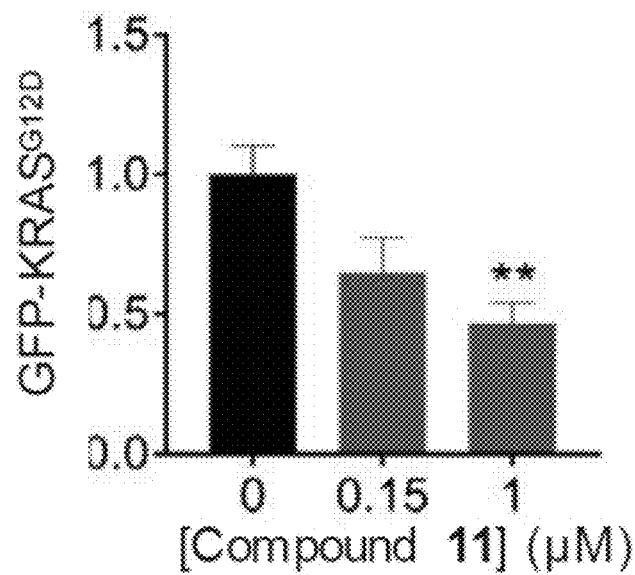
Figure 2C:
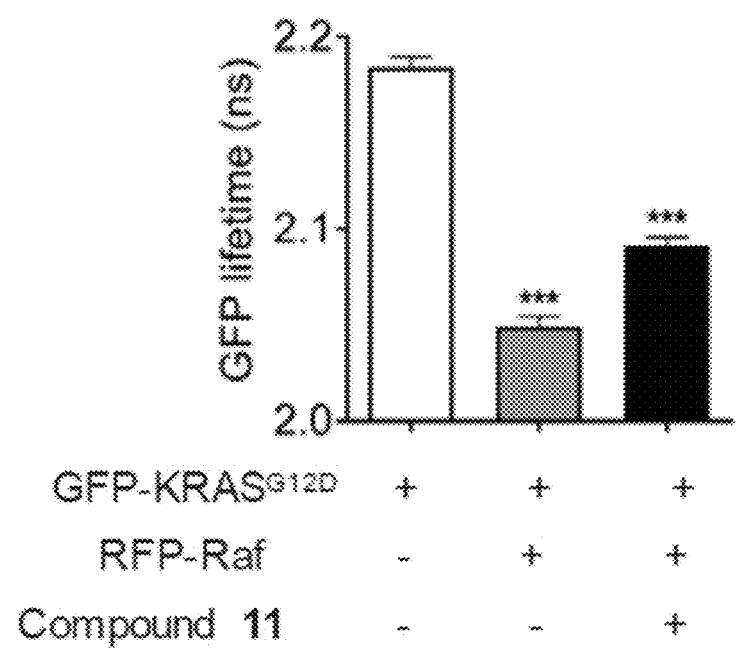

Compound 11 abolishes interaction of KRAS with Raf. Three different assays were used to check if the compound inhibits RAS signaling by interfering with effector binding. These included fluorescence polarization and pull-down assays, which directly measure the interaction of KRAS with the RBD of Raf in purified or cell lysate systems and FLIM-FRET, which measures the interaction of KRAS with full-length Raf in the cellular milieu. Fluorescence polarization of BGTP-γ-S was used to monitor binding of the KRAS catalytic domain to GST-Raf$^{RBD}$ with and without pre-incubation with 1 µM compound 11. FIG. 2A shows a dramatic decrease in polarization in the entire concentration range of GST-Raf$^{RBD}$. For example, at 2 µM GST-Raf$^{RBD}$, compound treatment reduced the polarization and therefore RAS-Raf interaction by >80%. The dissociation constant derived from the polarization curves indicate that 11 reduced the affinity of KRAS to Raf$^{RBD}$ by ~13-fold. Consistent with this observation, pull-down of GFP-KRAS$^{G12D}$ by GST-Raf$^{RBD}$ beads show a significant (e.g. >50% at 1 µM of 11) decrease in GFP-KRAS$^{G12D}$ levels (FIG. 2B). The data show a similar effect in FLIM-FRET experiments in cells. In this experiment, quenching of GFP fluorescence lifetime indicates KRAS$^{G12D}$-cRaf interaction in cells co-transfected with GFP-KRAS$^{G12D}$ and RFP-cRaf. Quenching of GFP fluorescence lifetime and hence KRAS$^{G12D}$-cRaf interaction is significantly reduced upon compound treatment (FIG. 2C). These observations are supported by a comparative analysis of available RAS-Raf structures and the predicted ligand-bound structure. For example, superposition of the predicted KRAS$^{G12D}$:11 complex onto HRAS:Raf (PDB 4G0N) structure shows that the piperazineethanol of 11, which interacts with E37 of KRAS, clashes with R67 of Raf (FIG. S2; see Appendix I, attached hereto). Taken together, these results strongly suggest that compound 11 inhibits MAPK signaling by directly disrupting RAS-effector interaction.

Figure 3:
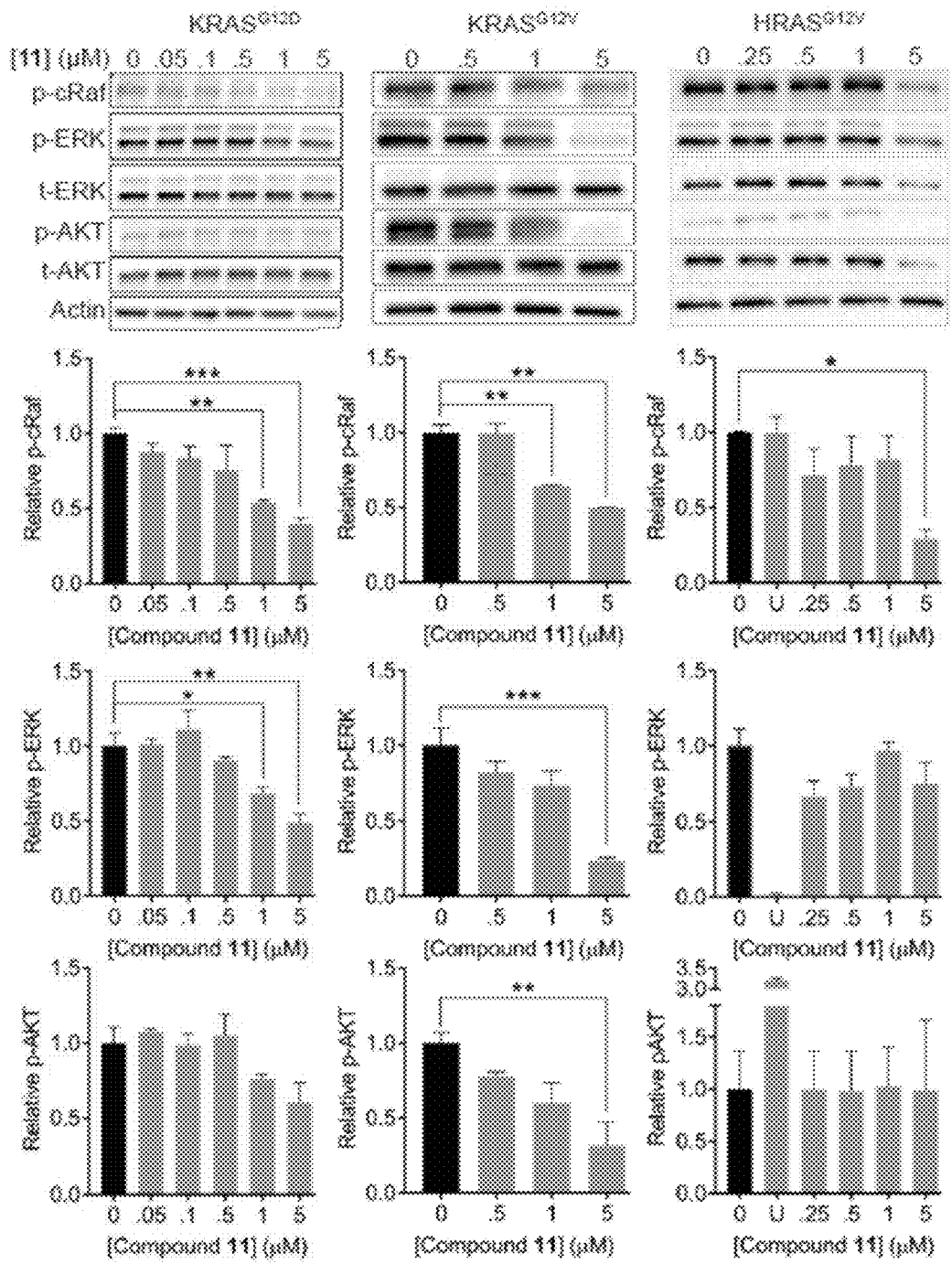
FIG. 3 shows representative data for the inhibition of mutant KRAS signaling by disclosed compound 11. Representative Western blots (top) and their quantification showing levels of phosphorylated cRaf (p-cRaf), ERK (p-ERK) and AKT (p-AKT) in cells expressing KRAS$^{G12D}$ (left), KRAS$^{G12V}$ (middle) and HRAS$^{G12V}$ (right) treated with the indicated concentrations of compound 11, DMSO or, where indicated 10 μM MEK inhibitor U0125 (U). Compound 11 dose-dependently reduced p-cRaf and p-ERK levels, and to a lesser extent p-AKT levels, in cells expressing KRAS$^{G12D}$ (estimated IC$_{50}$ 0.7 μM for p-cRaf and 1.3 μM for p-ERK) and KRAS$^{G12V}$, but not HRAS$^{G12V}$. Data are shown as mean ±S.E; significance was estimated by one-way analysis of variance: *=p<0.02; =p<0.005; *=p<0.0001.
Figure 4:
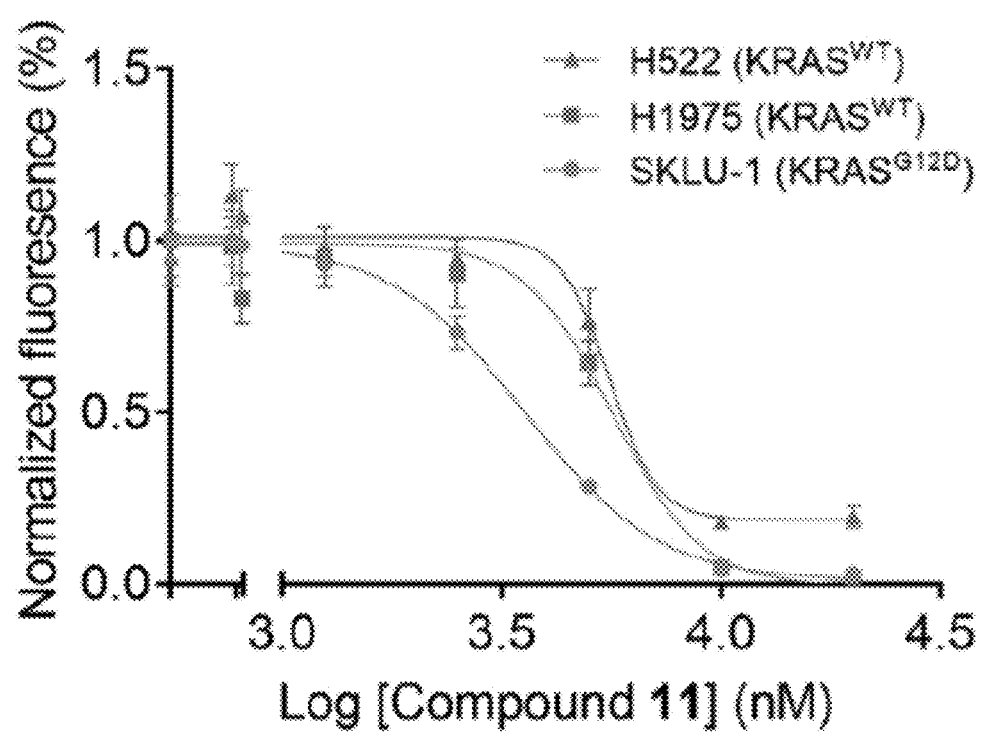
FIG. 4 shows representative proliferation assay data. Proliferation profile of lung cancer cells upon treatment by increasing concentration of compound 11 monitored by CyQuant assay. The cell line with mutant KRAS (SKLU-1) is slightly more sensitive than its KRAS$^{WT}$ counterparts H522 and H1975. The data suggest that cancer cells are sensitive to compound 11.

Compound 11 inhibits KRAS signaling. FIG. 3 shows that compound 11 dose-dependently decreases both p-ERK and p-cRaf levels in BHK cells expressing KRAS$^{G12D}$ and KRAS$^{G12V}$, suggesting inhibition of RAS signaling via the MAPK pathway. The data also indicate that the ligand has a slightly lower IC$_{50}$ for its direct effector cRaf (e.g., 0.7 µM in the case of KRAS$^{G12D}$) than the two-steps removed ERK (1.3 µM). Note also that the IC$_{50}$ for cRaf is very close to the $K_D$ of the ligand for $^{GTP}KRAS$. Changes in phosphorylated AKT (p-AKT) levels show that the compound also inhibits signaling through the AKT pathway but to a lesser extent than the MAPK pathway. Together, these results suggest that the ligand disrupts MAPK signaling by acting on RAS or its upstream modulators. To test if compound 11 is selective for the KRAS isoform, p-ERK and p-cRaf levels were measured in BHK cells expressing the constitutively active HRAS$^{G12V}$ (FIG. 3, right). The data show no significant effect on the phosphorylation of these effectors and hence signaling via the MAPK pathway. Similarly, no major effect on p-AKT levels was observed even though H-Ras is a major driver of the AKT pathway. As a control, treatment of the HRAS$^{G12V}$-expressing BHK cells with a 10 µM of the control U (the MEK inhibitor U0126) almost completely abolished MAPK signaling (FIG. 3). To test if the disclosed compounds affect proliferation of cancer cells, a CyQuant assay was used to assess effects in H1975 and H522 (KRAS$^{WT}$) and SKLU-1 (KRAS$^{G12D}$) lung cancer cells. FIG. 4 shows that each of these cells is sensitive to the compound, with SKLU-1 being especially responsive. Consistent with the binding data (FIG. 1D), there is no significant difference in the effect of 11 on KRAS$^{WT}$ and KRAS$^{G12D}$ lung cancer cells. In summary, the cell signaling and proliferation assays indicate that compound 11 selectively inhibits signaling through activated KRAS, which is consistent with its significant effect on KRAS-Raf interaction (FIG. 2).

Figure 5A:
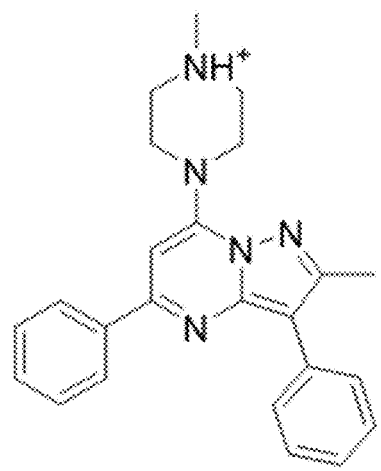
FIGS. 5A-5E show representative data demonstrating that the piperazinylethanol moiety of compound 11 is important for abrogating effector binding.
Figure 5B:
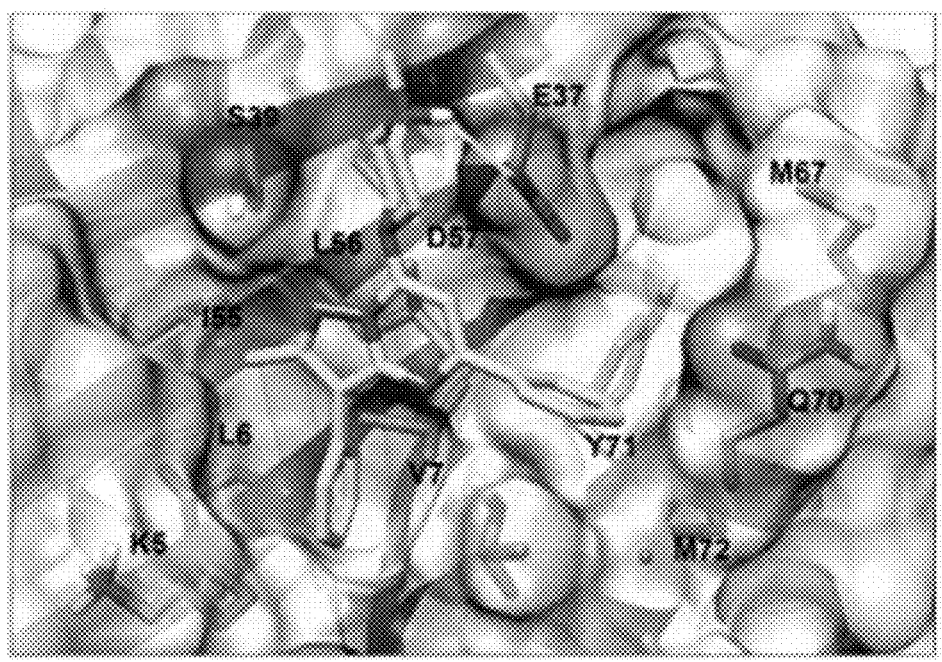
Figure 5C:
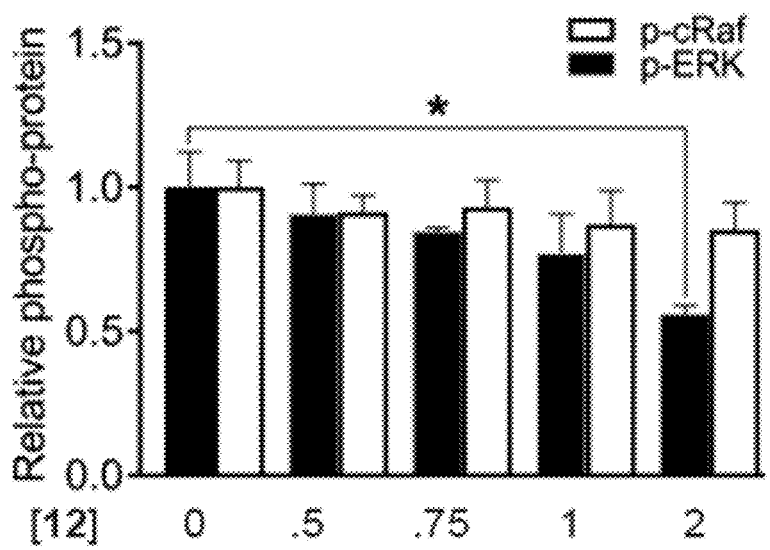
Figure 5D:
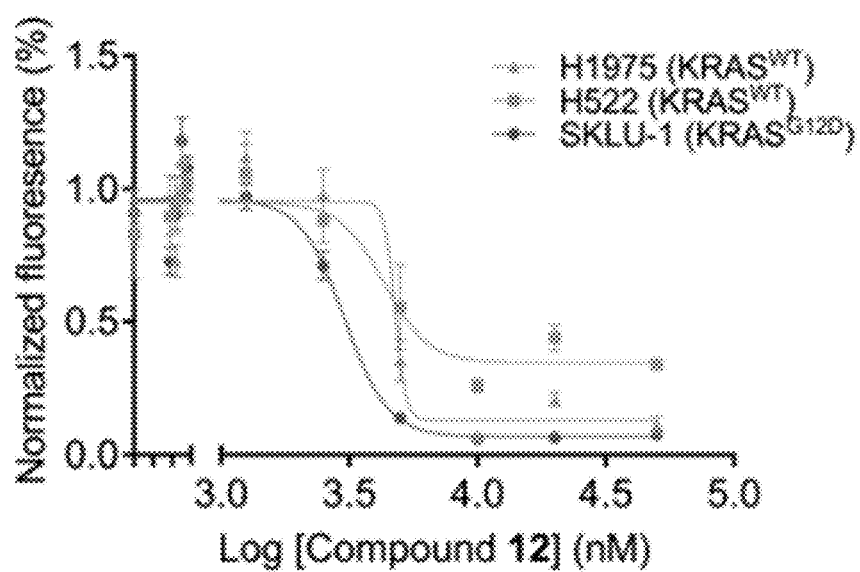
Figure 5E:
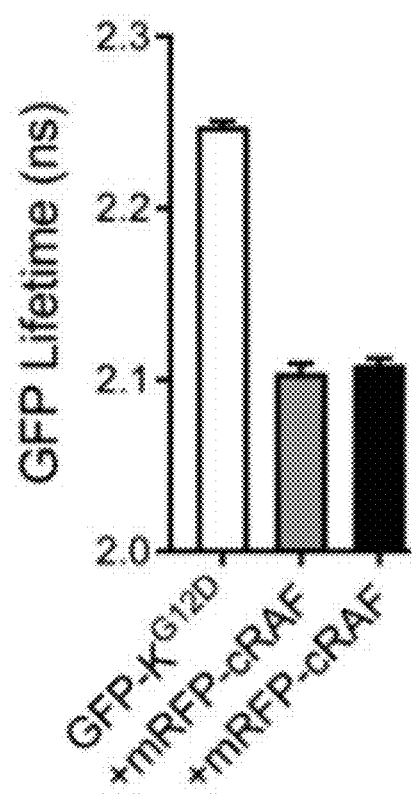

Mechanism of action and optimization route for pyrazolopyrimidine-based KRAS inhibitor. In addition to its effect on effector binding, compound 11 also slightly reduced the rates of both intrinsic and SOS-mediated GDP/GTP exchange reactions of KRAS, as well as SOS-mediated GDP release (SI text and FIGS. S3, S4). To identify the chemical fingerprints of compound 11 responsible for its high-affinity binding and dual-effect on KRAS function, compounds 12 and 13 were studied. Obtained from similarity searches based on 11, these analogues provided invaluable insights into the mechanisms of action of the disclosed pyrazolopyrimidine-based ligand. In compound 12, the 1-piperazineethanol functional group of 11 is replaced by 1-methylpiperazine (FIG. 5A,B), making it more hydrophobic and less soluble in DMSO. This compound reduced p-ERK levels at a slightly higher concentration of 2 µM (FIG. 5C), is somewhat less effective in inhibiting cell proliferation but exhibits a better selectively profile (FIG. 5D). However, compound 12 has no effect on p-cRaf levels (FIG. 5C), suggesting a different mechanism of inhibition than compound 11. These results were confirmed this by FLIM-FRET, which showed that compound 12 does not affect KRAS-Raf interaction (FIG. 5E). The predicted binding mode of compound 12 is very similar to that of 11, with the only difference being the lack of hydrogen bonding interactions with residues at the effector binding loop (FIG. 5B). Together, these results indicate that the ethanol moiety on the piperazine ring, which in compound 11 forms a hydrogen bond with E37 of the effector-binding loop (FIG. 10), is crucial for disrupting KRAS-Raf interaction.

Figure 6A:
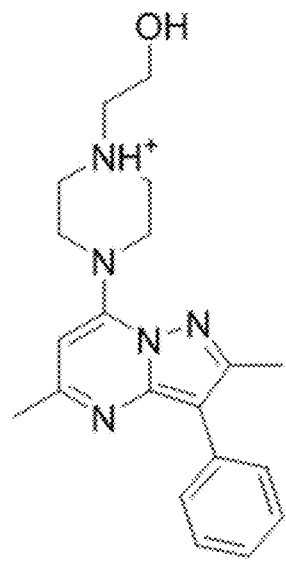
FIGS. 6A-6F show representative data demonstrating that interaction with switch 2 residues is important for modulating exchange factor activity.
Figure 6B:
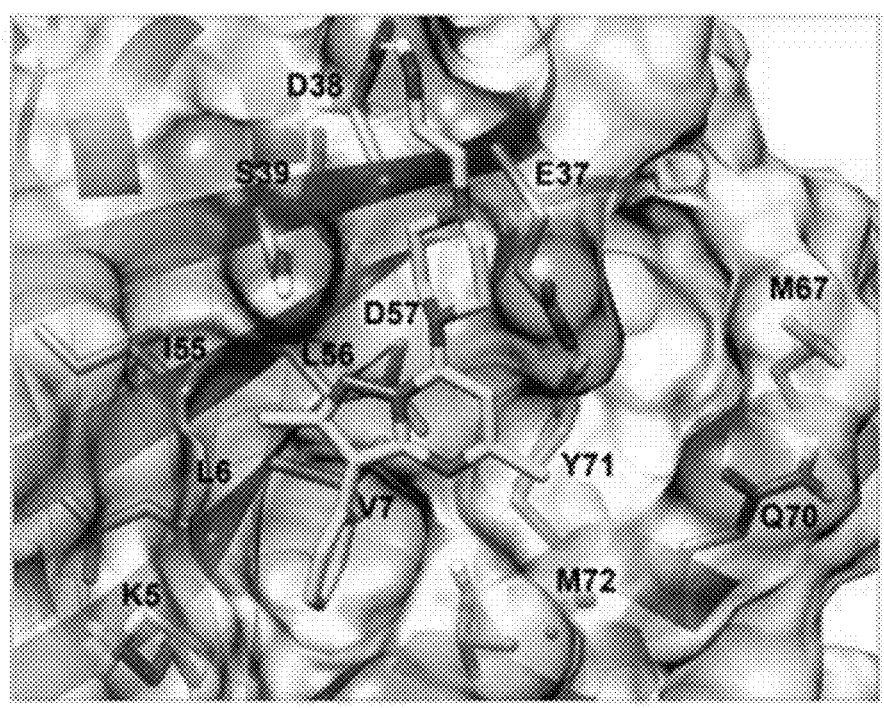
Figure 6C:
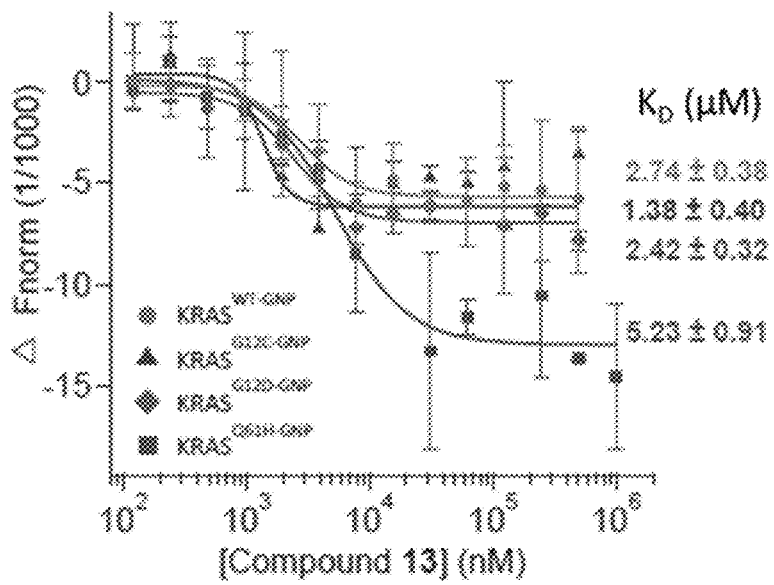

Despite its many attractive features, solubility issues made compound 12 difficult to work with; a compound with a better solubility profile would be desirable. Without wishing to be bound by a particular theory, it is believed that a derivative that preserves 11's effectiveness in inhibiting effector binding would provide improved activity with desirable therapeutic agent characteristics. As shown below compound 13 (FIGS. 6A and 6B) satisfies both of these conditions. It has a methyl group attached to the pyrimidine in place of the benzene ring found on 11, which makes it less hydrophobic and readily soluble in DMSO and other common solvents. Therefore, the $K_D$ of the interaction of compound 13 with G12D and other KRAS mutants using MST was measured. The results summarized in FIG. 6C show that this compound has a 6.5-7.1-fold weaker affinity for KRAS than compound 11. Similar to compound 11, however, 13 does not bind to $^{GDP}KRAS^{WT}$ or $^{GDP}KRAS^{G12D}$. Comparison of the docked poses of 11 (FIG. 1C) and 13 (FIG. 6B) provided a rationale for the observed differences in binding affinity. The benzene ring of compound 11 is involved in a T-shaped π-stacking interaction with the side chain of Y71, which is replaced by the much smaller methyl group in compound 13. Together, these findings demonstrate the critical role of the phenyl ring on the pyrimidine core for potency, providing a useful clue for future optimization efforts.

Figure 6D:
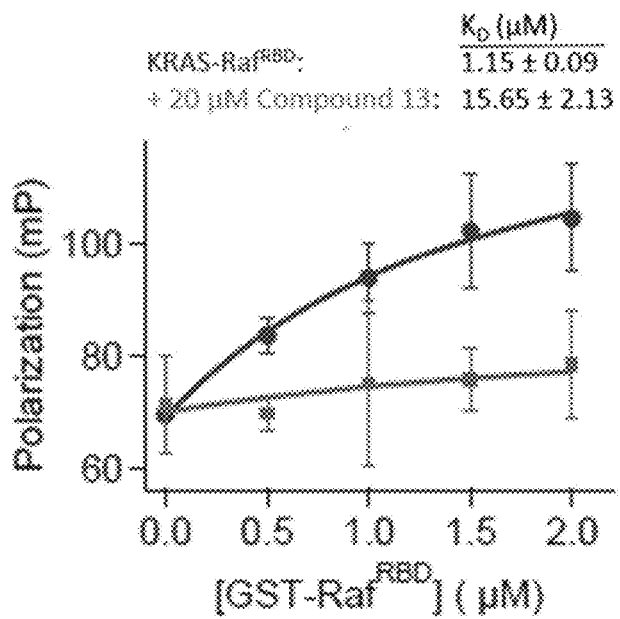
Figure 6E:
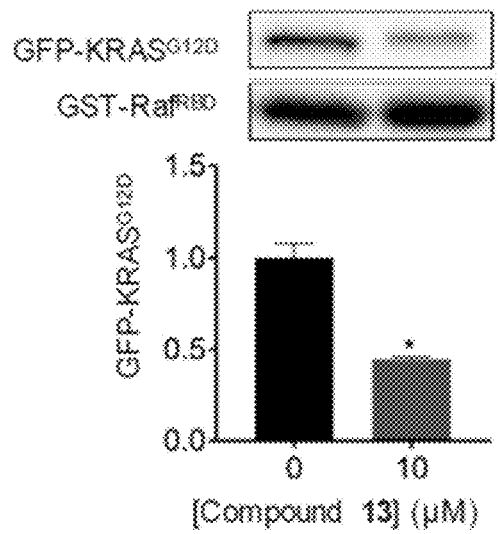

Fluorescence polarization and pull-down assays were then utilized to test the functional implication of the modification in compound 13 relative to the parent compound 11. FIG. 6D shows that 20 μM of 13 disrupts the interaction of KRAS with GST-Raf$^{RBD}$ as effectively as the parent compound. The pull-down assay led to the same conclusion: compound 13 disrupts KRAS$^{G12D}$-Raf$^{RBD}$ interaction (FIG. 6E). These results demonstrate that modifications can be made on the pyrazolopyrimidine core to optimize for potency without compromising effect on effector binding. This conclusion is supported by the structural analysis (FIGS. 1C and 6B), which shows that compounds 11 and 13 make identical contacts with residues at the effector-binding region via their piperazine ring and especially the piperazineethanol group. This is important because, as the data obtained herein using compound 12, modification in this part of the ligand causes loss of effect on Raf binding. In order to assess if interaction with switch 2 residues may play a role in nucleotide release, because the conformation of many switch 2 residues, such as Y71 and Y64, differs between free and GEF-bound RAS (51, 52), the intrinsic and SOS-dependent rates of labeled-GDP release in the absence and presence of compound 13 were determined.

The effect of compound 11 on intrinsic and GEF-dependent nucleotide release and exchange reactions was determined. In Appendix I, Figure S4 shows time-dependent decreases and increases of fluorescence intensity as a labeled-nucleotide dissociates from and binds to KRAS$^{WT}$, respectively. Compound 11 slightly reduced the rates of both intrinsic and SOS-mediated nucleotide exchange reactions, as well as the SOS-dependent (but not intrinsic) release of labeled-GDP. In particular, 11 decreased the intrinsic rate of nucleotide exchange by ~10-fold at >10 μM (FIG. S4, top-left), but it has no effect on intrinsic nucleotide release (Appendix I, Figure S4, bottom-left). The latter is consistent with the observation from MST that 11 does not bind to GDPKRASVVT with high affinity. Since GTP hydrolysis is unlikely to occur within the timescale of the experiments disclosed herein (2, 3), a plausible interpretation of the former would be compromised GTP loading. This is possible if, for example, the ligand binds to the nucleotide free 'transition state' conformation of KRAS and induces reorganization of active site residues. This is supported by the fact that 11's effect on the rate of nucleotide exchange is significantly smaller (only a 1.1-fold decrease, FIG. S4 top-right). SOS stabilizes nucleotide free RAS in an open active site conformation (4, 5), which allows for faster expulsion and rebinding of GTP or GDP.

Figure 6F:
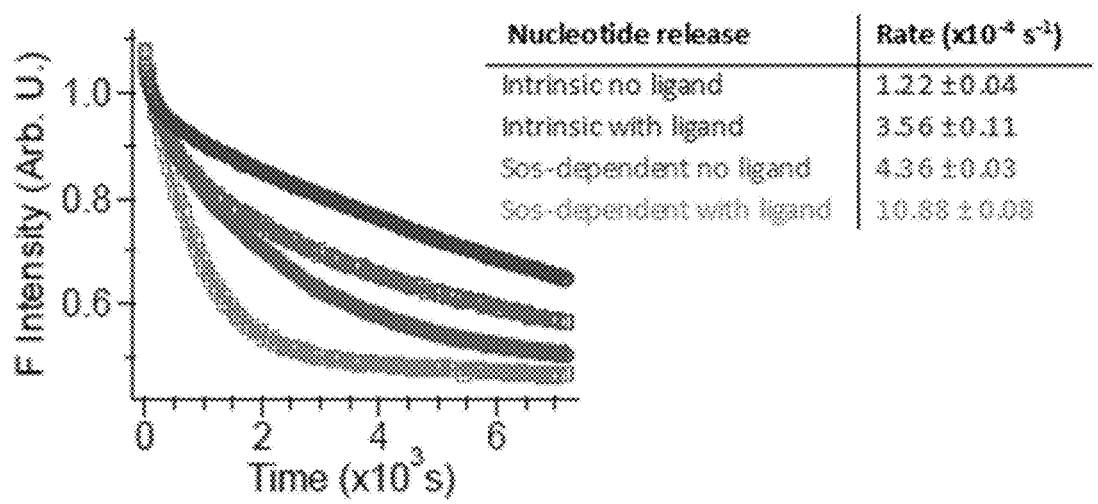
Figure 7:
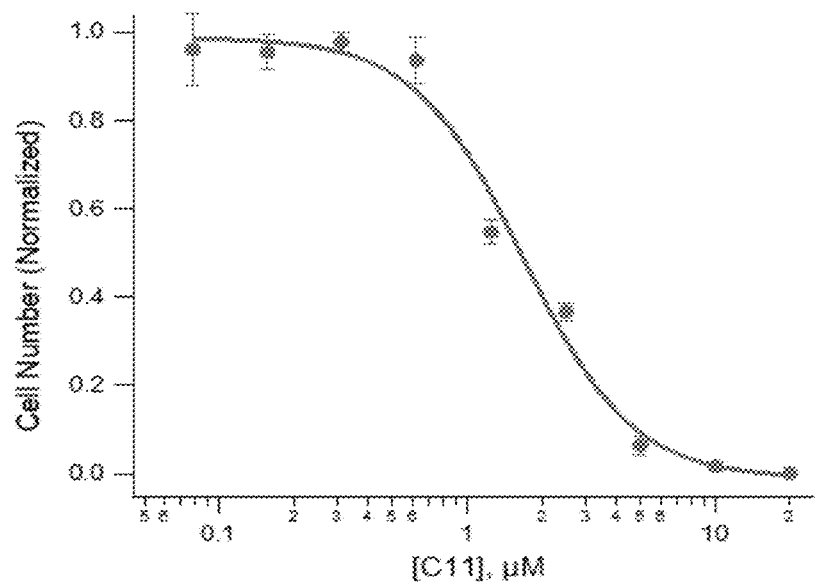
FIG. 7 shows representative data demonstrating of inhibition of the proliferation of RASless MEF cells expressing the oncogenic mutant kinase BRAF V600E using compound 11. Cell numbers were averaged from 3 independent measurements and normalized with respect to DMSO control. Assays were conducted as described in McCarthy et al, (ACS Omega2019, 4, 2, 2921-2930). The data shown were used to calculate $IC_{50}$ for inhibition of proliferation of 1.68±0.17 µM.
Figure 8:
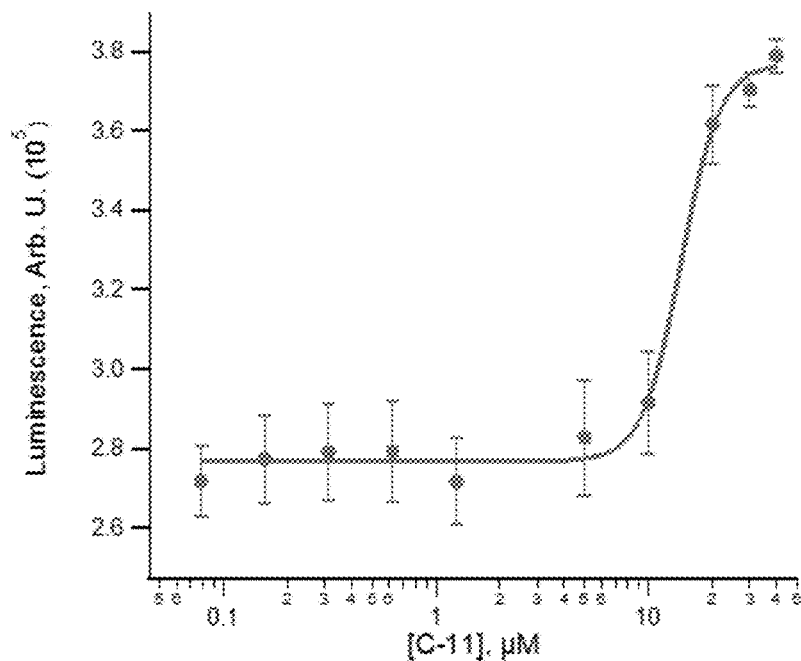
FIG. 8 shows representative data demonstrating inhibition of enzymatic activity of the constitutively active BRAF mutant V600E kinase. Activity was determined using Kinase Assay kit (BPS Bioscience, Inc., San Diego, Calif.; Cat. No. 48688) following the manufacturer's recommended protocol. The luminescence signal is directly proportional to the amount of remaining ATP and inversely proportional to kinase activity. The data shown were used to calculate $IC_{50}$ for inhibition of BRAF activity of 14.21±0.85 µM.

Whereas compound 11 had no effect on intrinsic and only modestly decreased the rate of SOS-mediated nucleotide release (see Appendix I, attached hereto, FIG. S4), compound 13 dramatically increased both rates (FIG. 6F). This result demonstrates that interaction with switch 2 residues including Y71 determines how a p1-bound ligand affects GEF activity. These results also provided strong support for the reliability of the predicted ligand-KRAS complex structures, and offered a viable route for additional modifications in future optimization efforts.

Finding a direct inhibitor of KRAS remains a major challenge in the search for cancer therapy. Previous attempts at preventing membrane binding of KRAS by farnesyl transferase inhibitors failed in clinical trials. More recent efforts focused on the dynamics of RAS revealed allosteric pockets suitable for binding of small molecules (33, 53). Several small-molecule ligands that bind to some of these pockets and disrupt interaction with GEFs or effectors have been discovered (21-25). However, thus far none of these ligands have led to a viable lead compound. In the present disclosure, a structure based computational design followed by biophysical and cell biological experiments to discover a novel high-affinity KRAS inhibitor, compound 11, that has unique structural features. Compound 11 (2-[4-(8-methyl-3, 9-diphenyl-2,6,7-triazabicyclo[4.3.0]nona-2,4,7,9-tetraen-5-yl)piperazin-1-yl]ethanol) is drug-like (drug-likeness=4.1) and somewhat polar with 6 hydrogen bond donors and 2 acceptors (cLogP=0.87). It has a pyrazolopyrimidine core rather than an indole or imidazole ring typical in the published ligands. Also, 11 is relatively large (415 Da) with its pyrazol ring methylated and benzylated and its pyrimidine ring beta-modified by benzene and 1-piperazineethanol. This allowed it to make more extensive contacts with KRAS residues than is common in most of the published ligands (FIG. 1C). As a result, compound 11 binds to KRAS at allosteric site p1 with nanomolar affinity and inhibits MAPK signaling and proliferation of KRAS-dependent cancer cells. Moreover, the fluorescence polarization, pull-down and FLIM-FRET assays demonstrated that compound 11 inhibits MAPK signaling primarily by abrogating interaction with effector proteins (FIG. 2), in contrast to many published KRAS ligands that primarily affect GEF activity (22-24). The data herein also show that the compound decreases intrinsic and SOS-mediated nucleotide exchange reactions. Comparative analyses of compound 11 and its analogues 12 and 13 allowed us to unambiguously determine the mechanisms by which 11 simultaneously abolishes effector binding and modulates intrinsic and GEF-mediated nucleotide exchange reactions. The analogues have a somewhat weaker (low μM) affinity for KRAS but exhibit enhanced selectivity. Importantly, they inhibit signaling via different mechanisms due to changes in a few protein-ligand interactions. In particular, the piperazineethanol group that interacts with switch 1 of KRAS was found to be critical for abrogating effector binding, whereas the switch 2-interacting nonpolar moieties attached to the pyrazolopyrimidine core modulate GEF activity. These observations provide an ideal platform for further optimization of the disclosed highly promising compounds.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for the treatment of a disease or disorder in a mammal in need thereof, comprising the step of administering to the mammal a pharmaceutical composition comprising a compound having a structure represented by a formula:

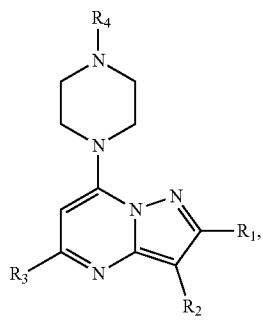

wherein R2 is aryl
wherein R1 is C1-C6 alkyl;
wherein R3 is a C1-C8 alkyl, cycloalkyl, heterocycloalkyl, aryl, or heteroaryl; and
wherein R4 is —(C1-C6 alkyl), —(C1-C6 alkanediyl)-OH,
or a pharmaceutically acceptable salt thereof, and a pharmaceutically acceptable carrier;
wherein the disease or disorder is cancer associated with abnormal, increased, or aberrant mutant KRAS activity.

2. The method of claim 1, wherein R1 is methyl.

3. The method of claim 1, wherein the disease or disorder is associated with abnormal, increased, or aberrant serine/threonine-protein kinase B-Raf activity.

4. The method of claim 1, wherein the cancer can be treated by inhibition of B Raf activity.

5. The method of claim 1, wherein the cancer is selected from selected from hematopoetic cancer, breast cancer, colorectal cancer, ovarian cancer, prostate cancer, pancreatic cancer, brain cancer, genitourinary tract cancer, lymphatic system cancer, stomach cancer, larynx cancer, and lung cancer.

6. The method of claim 1, wherein R3 is selected from C1-C8 alkyl and aryl.

7. The method of claim 6, wherein the compound is present as:

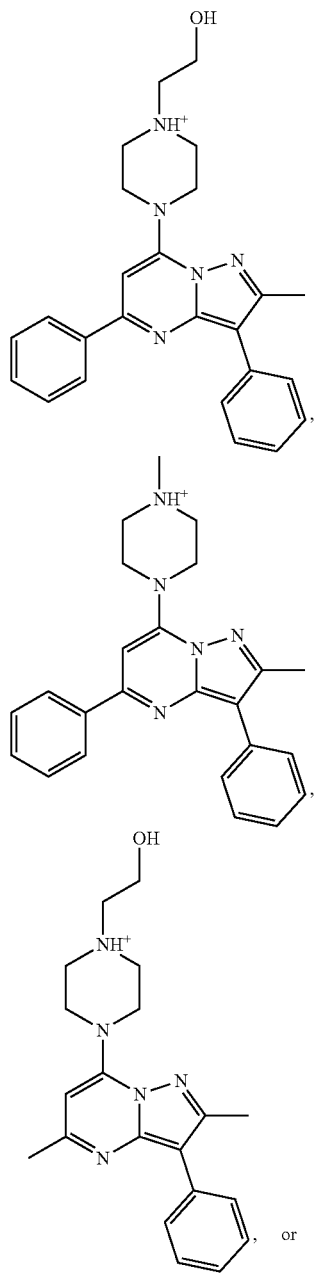

or combinations thereof.

* * * * *